United States Patent
Andrews

(10) Patent No.: US 8,382,672 B2
(45) Date of Patent: Feb. 26, 2013

(54) MACRO/MICRO DUTY CYCLE DEVICES, SYSTEMS, AND METHODS EMPLOYING LOW-FREQUENCY ULTRASOUND OR OTHER CYCLICAL PRESSURE ENERGIES

(76) Inventor: Claire Andrews, Menlo Park, CA (US)

( * ) Notice: Subject to any disclaimer, the term of this patent is extended or adjusted under 35 U.S.C. 154(b) by 10 days.

(21) Appl. No.: 13/047,626

(22) Filed: Mar. 14, 2011

(65) Prior Publication Data

US 2012/0065552 A1    Mar. 15, 2012

Related U.S. Application Data

(60) Provisional application No. 61/340,100, filed on Mar. 12, 2010.

(51) Int. Cl.
  *A61B 8/14* (2006.01)
(52) U.S. Cl. .................................. 600/459; 600/439
(58) Field of Classification Search .......... 600/437–469; 601/1–3
  See application file for complete search history.

(56) References Cited

U.S. PATENT DOCUMENTS

| | | | |
|---|---|---|---|
| 5,399,158 A | | 3/1995 | Lauer et al. |
| 5,509,896 A | | 4/1996 | Carter |
| 5,695,460 A | | 12/1997 | Siegel et al. |
| 5,873,855 A | * | 2/1999 | Eggers et al. .............. 604/114 |
| 5,879,314 A | | 3/1999 | Peterson et al. |
| 6,032,674 A | * | 3/2000 | Eggers et al. .............. 128/898 |
| 6,102,046 A | * | 8/2000 | Weinstein et al. .......... 128/898 |
| 6,435,037 B1 | * | 8/2002 | Doten .................... 73/861.27 |
| 6,539,316 B1 | * | 3/2003 | Doten et al. ................ 702/48 |
| 6,763,836 B2 | * | 7/2004 | Tasto et al. ................ 128/898 |
| 6,790,187 B2 | | 9/2004 | Thompson et al. |
| 6,805,130 B2 | * | 10/2004 | Tasto et al. ............... 128/898 |
| 7,220,232 B2 | | 5/2007 | Suorsa et al. |
| 7,229,423 B2 | | 6/2007 | Horzewski et al. |
| 7,241,270 B2 | | 7/2007 | Horzewski et al. |
| 7,335,169 B2 | * | 2/2008 | Thompson et al. .............. 601/2 |
| 7,517,328 B2 | | 4/2009 | Hoffmann |
| 7,645,244 B2 | | 1/2010 | Mason et al. |
| 7,727,863 B1 | * | 6/2010 | Buckalew et al. ............ 438/473 |
| 2002/0049395 A1 | | 4/2002 | Thompson et al. |
| 2002/0055693 A1 | | 5/2002 | Thompson et al. |
| 2002/0068930 A1 | * | 6/2002 | Tasto et al. ................... 606/32 |
| 2002/0072690 A1 | | 6/2002 | Thompson et al. |
| 2002/0072691 A1 | | 6/2002 | Thompson et al. |
| 2002/0082529 A1 | | 6/2002 | Suorsa et al. |
| 2002/0091339 A1 | | 7/2002 | Horzewski et al. |
| 2002/0151777 A1 | * | 10/2002 | Hynynen et al. .............. 600/407 |
| 2003/0050560 A1 | | 3/2003 | Suorsa et al. |
| 2003/0050576 A1 | | 3/2003 | Thompson et al. |
| 2003/0055363 A1 | | 3/2003 | Horzewski et al. |

(Continued)

OTHER PUBLICATIONS

Alpert et al., "Mapping of Local Renal Blood Flow with PET and $H_2^{15}O$", J. Nucl. Med., 2002, 43:470-475.

(Continued)

*Primary Examiner* — Sanjay Cattungal
(74) *Attorney, Agent, or Firm* — Kilpatrick Townsend and Stockton LLP

(57) ABSTRACT

Improved devices, systems, and methods treatment of patients can be used to help mitigate injury to the kidneys by applying cyclical mechanical pressure energy at low intensities. The energy often be selectively directed from non-invasive transducers disposed outside the patients. The energy will typically comprise low frequency ultrasound energy, shock wave energy, or the like, and may induce the generation and/or release of nitric oxide, thereby enhancing perfusion and ameliorating tissue damage. Superimposed micro and macro duty cycles may help avoid thermal and other injury to tissues of the patient during treatment. Bilateral treatments are facilitated by a support structure that orients at least one transducer toward each kidney.

16 Claims, 17 Drawing Sheets

U.S. PATENT DOCUMENTS

| | | | |
|---|---|---|---|
| 2003/0069526 A1 | 4/2003 | Thompson et al. | |
| 2003/0171743 A1* | 9/2003 | Tasto et al. | 606/32 |
| 2004/0073115 A1 | 4/2004 | Horzewski et al. | |
| 2004/0153009 A1 | 8/2004 | Horzewski et al. | |
| 2004/0253183 A1* | 12/2004 | Uber et al. | 424/9.52 |
| 2006/0189971 A1* | 8/2006 | Tasto et al. | 606/32 |
| 2007/0079455 A1* | 4/2007 | Brewer et al. | 15/22.2 |
| 2007/0157404 A1* | 7/2007 | Brewer et al. | 15/22.1 |
| 2007/0244415 A1 | 10/2007 | Horzewski et al. | |
| 2007/0265601 A1* | 11/2007 | Horzewski et al. | 606/1 |
| 2008/0027082 A1 | 1/2008 | Hocher et al. | |
| 2008/0064991 A1* | 3/2008 | Suorsa et al. | 601/2 |
| 2008/0167556 A1 | 7/2008 | Thompson et al. | |
| 2008/0195002 A1 | 8/2008 | Thompson et al. | |
| 2008/0208084 A1 | 8/2008 | Horzewski et al. | |
| 2008/0214938 A1* | 9/2008 | Solomon et al. | 600/459 |
| 2008/0319375 A1* | 12/2008 | Hardy | 604/22 |
| 2009/0318813 A1* | 12/2009 | Thompson et al. | 600/459 |
| 2010/0022875 A1 | 1/2010 | Horzewski et al. | |
| 2010/0049100 A1 | 2/2010 | Horzewski et al. | |
| 2010/0100015 A1 | 4/2010 | Mason et al. | |
| 2010/0125198 A1* | 5/2010 | Thapliyal et al. | 600/439 |
| 2011/0092781 A1 | 4/2011 | Gertner | |
| 2012/0065501 A1 | 3/2012 | Dae et al. | |

OTHER PUBLICATIONS

Altland et al., "Low-intensity Ultrasound Increases Endothelial Cell Nitric Oxide Synthase Activity and Nitric Oxide Synthesis", Journal of Thrombosis and Haemostasis, 2004, 2:637-43.

Atar et al., "Ultrasound at 27 kHz Increases Tissue Expression and Activity of Nitric Oxide Synthases in Acute Limb Ischemia in Rabbits", Ultrasound in Med. & Biol., 2007, 33(9):1483-1488.

Bachmann et al., "Nitric Oxide in the Kidney: Synthesis, Localization, and Function", American Journal of Kidney Diseases, 1994, 24:112-129.

Basile, "The Endothelial Cell in Ischemic Acute Kidney Injury: Implications for Acute and Chronic Function", Kidney International, 2007, 72:151-56.

Blankestijn, "Sympathetic Hyperactivity—A Hidden Enemy in Chronic Kidney Disease Patients", Peritoneal Dialysis International, vol. 27, 2007, Supplement 2, pp. S293-S297.

Brinton et al., "Ultrasound Mediated Renal Sympathetic Denervation", Circulation, 124:Abstract 12272, 2011.

Christman et al., "Enhanced Neovasculature Formation in Ischemic Myocardium Following Delivery of Pleiotrophin Plasmid in a Biopolymer", Biomaterials, 2005, 26:1139-1144.

Christman et al., "Fibrin Glue Alone and Skeletal Myoblasts in a Fibrin Scaffold Preserve Cardiac Function after Myocardial Infarction", Tissue Engineering, 2004, 10(3/4):403-409.

Christman et al., "Injectable Fibrin Scaffold Improves Cell Transplant Survival, Reduces Infarct Expansion, and Induces Neovasculature Formation in Ischemic Myocardium", J. Am. Coll. Cardiol., 2004, 44:654-660.

Contreras et al., "The Role of Nitric Oxide in the Post-Ischemic Revascularization Process", Pharmacology & Therapeutics, 2006, 112:553-563.

Cooke et al., "Nitric Oxide and Angiogenesis", Circulation, 2002, 105:2133-2135.

Da Silva, et al., "Absolute Quantification of Regional Myocardial Uptake of $^{99m}$Tc-Sestamibi with SPECT: Experimental Validation in a Porcine Model", Journal of Nuclear Medicine, 2001, 42:772-779.

Dae et al., "Effect of Endovascular Cooling on Myocardial Temperature, Infarct Size, and Cardiac Output in Human-Sized Pigs", Am. J. Physiol. Heart Circ. Physiol., 2002, 282:H1584-H1591.

Dae et al., "Scintigraphic Assessment of Sympathetic Innervation after Transmural Versus Nontransmural Myocardial Infarction", J. Am. Coll. Cardiol., 1991, 17:1416-1423.

De Groot et al., "Magnitute and Time Course of Arterial Vascular Adaptations to Inactivity in Humans", Exercise and Sport Sciences Reviews, 2006, 34(2): 65-71.

Elmstahl et al., "Nephrotoxicity after Renal Angiography Using Iodine and Gadolinium Contrast Media in Pigs with Renal Damage", Academic Radiology, 2002, 9(suppl 2):S531-S534.

Fisher et al., "Therapeutic Strategies for Targeting Excessive Central Sympathetic Activation in Human Hypertension", Experimental Physiology, 2010, 95.5, pp. 572-580.

Goldfarb et al., "Contrast-Induced Acute Kidney Injury: Specialty-Specific Protocols for Interventional Radiology, Diagnostic Computed Tomography Radiology, and Interventional Cardiology", Mayo Clinic Proceedings, 2009, 84(2):170-179.

Heyman et al., "Reactive Oxygen Species and the Pathogenesis of Radiocontrast-Induced Nephropathy", Investigative Radiology, 2010, 45:188-195.

Hong et al., "Nitric Oxide Reduces Flow-Induced Superoxide Production via cGMP-Dependent Protein Kinase in Thick Ascending Limbs", Am. J. Physiol. Renal Physiol., 2009, 296:F1061-F1066.

Huang et al., "Injectable Biopolymers Enhance Angiogenesis after Myocardial Infarction", Tissue Engineering, 2005, 11(11/12):1860-1866.

Iida et al., "Noninvasive Low-Frequency Ultrasound Energy Causes Vasodilation in Humans", Journal of the American College of Cardiology, 2006, 48:532-537.

Kornowski et al., "Does External Ultrasound Accelerate Thrombolysis? Results From a Rabbit Model", Circulation, 1994, 89:339-344.

Kupatt et al., "Endothelial Nitric Oxide Synthase Overexpression Provides a Functionally Relevant Angiogenic Switch in Hibernating Pig Myocardium", J. Am. Coll. Cardiol., 2007, 49:1575-1584.

Lee et al., "VEGF Gene Delivery to Myocardium: Deleterious Effects of Unregulated Expression", Circulation, 2000, 102:898-901.

Leonard et al., "VEGF-121 Preserves Renal Microvessel Structure and Ameliorates Secondary Renal Disease Following Acute Kidney Injury", Am. J. Physiol. Renal Physiol., 2008, 295:F1648-F1657.

Lerman et al., "Angiogenesis in the Kidney: A New Therapeutic Target?", Current Opinion in Nephrology and Hypertension, 2009, 18:160-165.

Liu et al., "Attenuation of Reperfusion Injury by Renal Ischemic Postconditioning: The Role of NO", Biochemical and Biophysical Research Communications, 2007, 359:628-634.

Misra et al., "The Porcine Remnant Kidney Model of Chronic Renal Insufficiency", Journal of Surgical Research, 2006, 135:370-379.

Myers et al., "Iodinated Contrast Induced Renal Vasoconstriction is Due in Part to the Downregulation of Renal Cortical and Medullary Nitric Oxide Synthesis", Journal of Vascular Surgery, 2006, 44:383-391.

Nishida et al., "Extracorporeal Cardiac Shock Wave Therapy Markedly Ameliorates Ischemia-Induced Myocardial Dysfunction in Pigs in Vivo", Circulation, 2004, 110:3055-3061.

Phillips et al., "Nitric Oxide Mechanism of Protection in Ischemia and Reperfusion Injury", Journal of Investigative Surgery, 2009, 22:46-55.

Riggs et al., "Ultrasound Enhancement of Rabbit Femoral Artery Thrombolysis", Cardiovascular Surgery, 1997, 5(2):201-207.

Sendeski et al., "Iodixanol, Constriction of Medullary Descending Vasa Recta, and Risk for Contrast Medium-Induced Nephropathy", Radiology, 2009, 251:697-704.

Siddiqi et al., "Is Kidney Ischemia the Central Mechanism in Parallel Activation of the Renin and Sympathetic System?", Journal of Hypertension, 2009, vol. 27, pp. 1341-1349.

Siegel et al., "Noninvasive, Transthoracic, Low-Frequency Ultrasound Augments Thrombolysis in a Canine Model of Acute Myocardial Infarction", Circulation, 2000, 101:2026-2029.

Siegel et al., "Ultrasound Energy Improves Myocardial Perfusion in the Presence of Coronary Occlusion", Journal of the American College of Cardiology, 2004, 44(7):1454-1458.

Snyder et al., "Prevalence of CKD in the United States: A Sensitivity Analysis Using the National Health and Nutrition Examination Survey (NHANES) 1999-2004", Am. J. Kidney Dis., 2009, 53(2):218-228.

Solomon, "Contrast-Induced Acute Kidney Injury (CIAKI)", Radiol. Clin. N. Am., 2009, 47:783-788.

Springer, "A Balancing Act: Therapeutic Approaches for the Modulation of Angiogenesis", Current Opinion in Investigational Drugs, 2006, 7(3):243-250.

Suchkova et al., "Effect of 40-kHz Ultrasound on Acute Thrombotic Ischemia in a Rabbit Femoral Artery Thrombosis Model", Circulation, 2000, 101:2296-2301.

Suchkova et al., "Ultrasound Improves Tissue Perfusion in Ischemic Tissue through a Nitric Oxide Dependent Mechanism", Thromb. Haemost., 2002, 88:865-870.

Sugita et al., "Nitric Oxide Generation Directly Responds to Ultrasound Exposure", Ultrasound in Med. & Biol., 2008, 34(3):487-493.

Sullivan et al., "Renal NOS Activity, Expression, and Localization in Male and Female Spontaneously Hypertensive Rats", Am. J. Physiol. Regul. Integr. Comp. Physiol., 2010, 298:R61-R69.

Traub et al., "Laminar Shear Stress: Mechanisms by Which Endothelial Cells Transduce an Atheroprotective Force", Arterioscler. Thromb. Vasc. Biol., 1998, 18:677-685.

Wu et al., "Quantification of Nitric Oxide Synthase Activity in Microdissected Segments of the Rat Kidney", Am. J. of Physiology, 1999, 276:F874-F881.

Yamashita et al., "Role of Nitric Oxide in the Renal Protective Effects of Ischemic Preconditioning", J. Cardiovasc. Pharmacol., 2003, 42:419-427.

Zhong et al., "Response of Descending Vasa Recta to Luminal Pressure", Am. J. Physiol. Renal Physiol., 2004, 287:F535-F542.

* cited by examiner

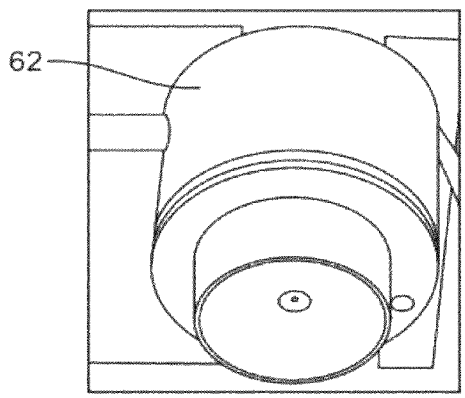
FIG. 16
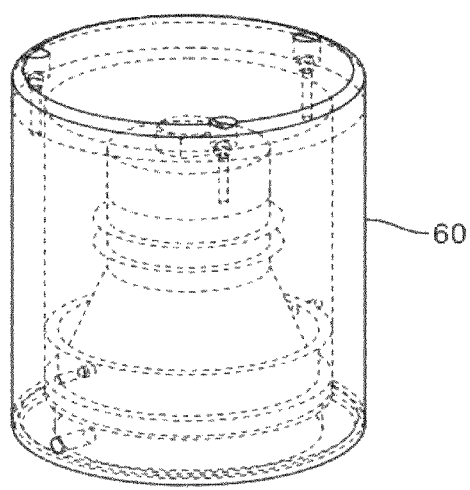 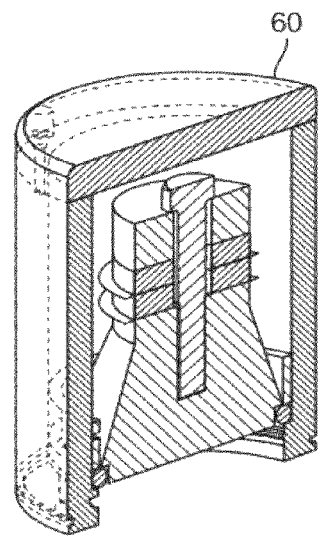
FIG. 17A          FIG. 17B

MACRO/MICRO DUTY CYCLE DEVICES, SYSTEMS, AND METHODS EMPLOYING LOW-FREQUENCY ULTRASOUND OR OTHER CYCLICAL PRESSURE ENERGIES

CROSS-REFERENCES TO RELATED APPLICATIONS

The present application claims the benefit under 35 USC 119(e) of U.S. Provisional Application No. 61/340,100 filed Mar. 12, 2010; the full disclosure of which is incorporated herein by reference in its entirety for all purposes. The subject matter of this application is related to that of an application entitled "Renal Injury Inhibiting Devices, Systems, and Methods Employing Low-Frequency Ultrasound or Other Cyclical Pressure Energies" application Ser. No. 13/047,618 filed concurrently with the present application; the full disclosure which is incorporated herein by reference.

STATEMENT AS TO RIGHTS TO INVENTIONS MADE UNDER FEDERALLY SPONSORED RESEARCH AND DEVELOPMENT

Not Applicable

FIELD OF THE INVENTION

The present invention relates generally to medical devices, systems, and methods. Exemplary embodiments provide devices, systems, and methods for applying cyclical mechanical pressure energy (such as low frequency ultrasound) so as to inhibit or ameliorate injury to a tissue of a patient. Specific embodiments provide devices, systems, and methods for avoiding or reducing substance-induced renal damage during contrast imaging or the like; and devices, systems, and methods to inhibit injury from chronic kidney disease for dialysis patients.

BACKGROUND OF THE INVENTION

Chronic kidney disease affects millions of patients, and has shown an increased prevalence in recent years. End-stage kidney disease alone affects hundreds of thousands of patients, and the numbers of these patients may double within the next 15 years. Chronic renal diseases can be complicated by progressive fibrosis and deterioration of renal function, and often ultimately results in irreversible renal failure. Treatment options for end-stage renal diseases typically involve repeated and time consuming dialysis procedures or kidney transplantation.

While much of the alarming increase in chronic and end-stage kidney disease relates to the rise in prevalence of obesity, diabetes, hypertension, and other cardiovascular risk factors, the kidneys are also subject to injury from additional sources. Acute kidney injury related to imaging procedures in which contrast media is administered to the patient appears to be one of the leading causes of hospital acquired renal failure. The deleterious effects of contrast media on the kidneys may be linked to increased lengths of hospital stays, higher rates of in-hospital cardiovascular events and increased mortality. Patients with pre-existing renal dysfunction and microvascular insufficiency are particularly vulnerable to the dangers of contrast-induced injury to the kidneys. Unfortunately, the population of patients with compromised kidneys that may be placed at risk by imaging procedures includes many of the same individuals whose lives may be saved and/or improved through the benefits of interventional cardiovascular and other therapies that are made possible through the use of contrast-enhanced imaging. As a result, millions of patients may be at risk for contrast-induced acute or chronic kidney injury.

Attempts to reduce or prevent contrast medium-induced renal failure have included periprocedural hydration, forced diuresis, blood volume expansion, low osmolality versus high osmolality contrast agents, dopamine, calcium channel blockers, mannitol, atrial natriuretic peptide, acetylcholine esterase (ACE) inhibitors, the adenosine antagonist theophylline, endothelin receptor antagonists, and N-acetylcysteine. None of these attempts has been fully effective. Contrast induced acute kidney injury remains a leading cause of iatrogenic acute kidney injury, despite adherence to protocols of risk assessment and prevention strategies.

In light of the above, it would be beneficial to provide improved devices, systems, and methods for treating patients. It would be particularly beneficial if these improved structures and techniques could be used to help mitigate the injury suffered by the kidneys of patients having chronic and/or acute renal disease. It would also be desirable for such benefits to be provided without excessively increasing the time and costs of life-preserving dialysis treatments, while helping to maintain (or even increase) the quality of life of dialysis patients.

BRIEF SUMMARY OF THE INVENTION

The present invention generally provides improved medical devices, systems, and methods for treatment of patients. Exemplary embodiments of these structures and techniques can be used to help mitigate and/or avoid injury to the kidneys. Advantageously, such injuries may be inhibited by applying cyclical mechanical pressure energy at low intensities to the kidneys, with the energy often be selectively directed from non-invasive transducers disposed outside the patient. The non-ablative energy levels may be so low as to be more commonly associated with imaging than significant therapeutic effects, thereby facilitating safe penetration through intervening tissues and throughout much or all of the tissue of the kidneys. While the energy will typically comprise, low frequency ultrasound energy, alternative embodiments may employ low intensity shock wave energy or the like. The energy will often induce the generation and/or release of nitric oxide, thereby enhancing perfusion and ameliorating tissue damage. Superimposed micro and macro duty cycles may help avoid thermal and other injury to tissues of the patient during treatment times that may extend from more than about 15 minutes to as much as 6 hours or more. Bilateral treatments are facilitated by a support structure that orients at least one transducer toward each kidney, and the treatment times may overlap (though not necessarily completely) with a dialysis procedure. Patients having compromised kidney function such that they would not otherwise meet established criteria for contrast imaging may be able to safely undergo life-preserving contrast image-guided therapies through the application of appropriate energy before, during, and/or after imaging; often without having to resort to overnight hydration or the like prior to administration of contrast agents.

In a first aspect, the invention provides a method for treating a patient. The patient is subjected to a procedure associated with injury of a kidney. The method comprises transmitting cyclical mechanical pressure energy from a transducer to the kidney. The energy can be transmitted to the kidney during a treatment time period and with a treatment energy level. The treatment time period corresponds to a time of the procedure associated with the potential injury of the kidney, and the treatment energy level is sufficient to inhibit the injury to the kidney.

In another aspect, the invention provides a method for treating a patient. The patient has first and second kidneys, and is subjected to an imaging procedure including administering of nephrotoxic contrast agent associated with a potential injury of the kidneys. The method comprises transmitting cyclical mechanical pressure energy from a first transducer selectively to the first kidney. The cyclical mechanical pressure energy is also transmitted from a second transducer selectively to the second kidney. The energy is transmitted to the kidneys for a treatment time period corresponding to a time of administering the nephrotoxic contrast agent so as to inhibit the potential injury to the kidney.

In another method aspect, the invention provides a method for treating a dialysis patient. The patient has first and second kidneys and is subjected to a plurality of dialysis procedures associated with injury of the kidneys. The method comprises transmitting cyclical mechanical pressure energy from a first transducer selectively to the first kidney. The cyclical mechanical pressure energy is transmitted from a second transducer selectively to the second kidney. The energy is transmitted to the kidneys for a plurality of treatment time periods, each time period overlapping with a time period of an associated dialysis procedure so that the progressive loss of kidney function is inhibited.

In a system aspect, the invention provides a system for treating a patient. The patient is subjected to a procedure associated with a potential injury of first and second kidneys of the patient. The system comprises a device having a body configured for receiving the patient. A first transducer is oriented by the body so as to selectively direct cyclical mechanical pressure energy to the first kidney when the body receives the patient. A second transducer is oriented by the body so as to selectively direct cyclical mechanical pressure energy to the second kidney when the body engages the patient and while the first transducer is oriented toward the first kidney.

In yet another aspect, the invention provides a method for treating a patient having a kidney with chronic kidney disease. The method comprises transmitting cyclical mechanical pressure energy selectively to the kidney. The energy is transmitted to the kidneys for a plurality of treatment time periods distributed over more than 2 weeks so that progressive loss of kidney function is inhibited.

In yet one more aspect, the invention provides a method for treating a patient. The patient has a tissue subject to injury, and the method comprises transmitting low frequency ultrasound energy from a transducer to the tissue. The energy is transmitted to the tissue during a treatment time period with a treatment energy level per a first duty cycle and a second duty cycle. The first duty cycle has a first repetition frequency and the second duty cycle has a repetition frequency different than the first duty cycle. The second duty cycle being superimposed on the first duty cycle. The treatment time period and energy level being sufficient to mitigate the injury to the tissue.

In another system aspect, the invention provides a system for treating a patient. The patient has tissue subject to injury. The system comprises a transducer configured to selectively direct low frequency ultrasound energy to the tissue. A power is source coupled to the transducer, the power source configured to energize the transducer for a treatment time period and with a treatment energy level per a first duty cycle and a second duty cycle. The first duty cycle has a first repetition frequency and the second duty cycle having a repetition frequency different than the first duty cycle. The second duty cycle is superimposed on the first duty cycle, and the treatment time period and energy level are sufficient to mitigate the injury to the tissue.

In many embodiments, the treatment energy level will be insufficient to induce ablation of the kidney. When nephrotoxic contrast agent agents or the like will be administered, potentially resulting in acute and/or progressive deterioration in renal function, the treatment time will often be within a day of the imaging procedure so that the energy mitigates nephrotoxicity of the contrast agent such that the acute and/or progressive deterioration is inhibited. Advantageously, even though the patient does not meet a kidney function criteria threshold for receiving contrast media, the application of the energy may alter the threshold so as to allow the imaging procedure to be performed. For example, a patient with an estimated Glomerular Filtration Rate (eGFR) score below 60 (indicating kidney damage) might otherwise be subjected to hydration, significantly delaying treatment. A patient with an eGFR score below 45 might otherwise be denied a therapy that involves the use of contrast media. With application of the energy before, during, and/or after administration of the contrast media the procedure may be allowed to proceed before the time that would otherwise have to be dedicated to hydration was completed. Hence, hydration delays may be decreased or avoided altogether, and imaging procedures may be performed on patients that otherwise would not yet meet the kidney function threshold.

When the procedure to which the patient will be subjected involves dialysis, the injury to the kidney will typically be the result of chronic kidney disease of the patient. Such conditions are associated with progressive loss of kidney function. In such embodiments, the treatment time will often be within a day of the dialysis procedure so that the progressive loss of kidney function is inhibited. As such patients are often subjected to many lengthy dialysis procedures, the energy can be transmitted to the kidney for treatment time periods that overlap with a dialysis period of an associated dialysis procedure. Note that the dialysis and energy delivery need not necessarily overlap for the full treatment time period and/or the full dialysis period.

The injury will often comprise ischemia of a tissue of the kidney. A non-invasive transducer can selectively direct the energy from outside the patient, via intermediate tissues of the patient between the transmission source and the kidney, and into the tissue of the kidney. The energy can inhibit the ischemia by significantly increasing perfusion within the tissue. The energy is selectively transmitted to most or all of the medulla of the kidney, and may be selectively transmitted to most or all of the kidney, often being selectively transmitted to both kidneys.

A first transducer may transmit the energy to the first kidney and a second transducer may transmit the energy to the other kidney from, the first and second transducers being disposed outside the patient during transmission of the energy. The treatment time period for the first kidney may overlap with a treatment time period for the second kidney, the first transducer being aligned with the first kidney simultaneously with alignment of the second transducer with the second kidney. In many embodiments, a support structure will support the first and second transducers and maintaining the simultaneous alignment. A body of the support structure may be configured for supporting the patient thereon in a sitting, prone, and/or supine position. In other embodiments, the body can be configured to be worn by the patient, allowing the patient to move and maintaining alignment between the transducers and the kidney or kidneys. In either case, the body often configured (via body-engaging surface contours, visible indicia such as instructions or graphical markers, or the like) to align the patient with the transducers.

While in some embodiment the energy may comprise low intensity shock waves, the energy typically comprises ultrasound energy. Exemplary embodiments employ low frequency ultrasound energy with a frequency in a range from about 20 kHz to about 500 kHz, an intensity of less than 3 watts/cm2, and/or a first duty cycle of 50% or less so that the transducer is energized for only a portion of the treatment time period. The first duty cycle may have a first duty cycle repetition frequency in a range from about 20 to about 50 Hz, optionally being about 35 Hz. This first duty cycle repetition frequency can define a series of first duty cycle time periods during the overall treatment time period. The transducer may be energized during a portion of each first time period per the first duty cycle throughout a portion of the treatment time period. A second duty cycle repetition frequency may similarly define a series of second duty cycle time periods during the overall treatment time period. The transducer may be selectively energized during only a portion of each second time interval. The second duty cycle can be superimposed on the first duty cycle, and the energized portions of the second time periods may be significantly longer than the first time periods so that during the energized portion of each second time period the energizing of the transducer repeatedly cycles per the first duty cycle. For example, when the first duty cycle repetition frequency is in a range from about 20 Hz to about 50 Hz (with this first, relatively rapid duty cycle sometimes being referred to as a micro duty cycle), the second time period of the second duty cycle may be much longer, optionally being between 2 and 30 minutes (with this second, much longer time-domain duty cycle sometimes being referred to as a macro duty cycle). Exemplary treatment time periods may be between ½ hour and about 6 hours, and will often include at least 4 macro duty cycles.

BRIEF DESCRIPTION OF THE DRAWINGS

FIG. 11 schematically shows acute application of LOFUS to protect the kidney for prevention of CI-AKI or the like;

FIG. 16 illustrates a LOFUS transducer for use with the generator of FIG. 15; and FIGS. 17A and 17B schematically illustrate an alternative LOFUS transducer for treatment of the kidneys.

DETAILED DESCRIPTION OF THE INVENTION

Figure 1:
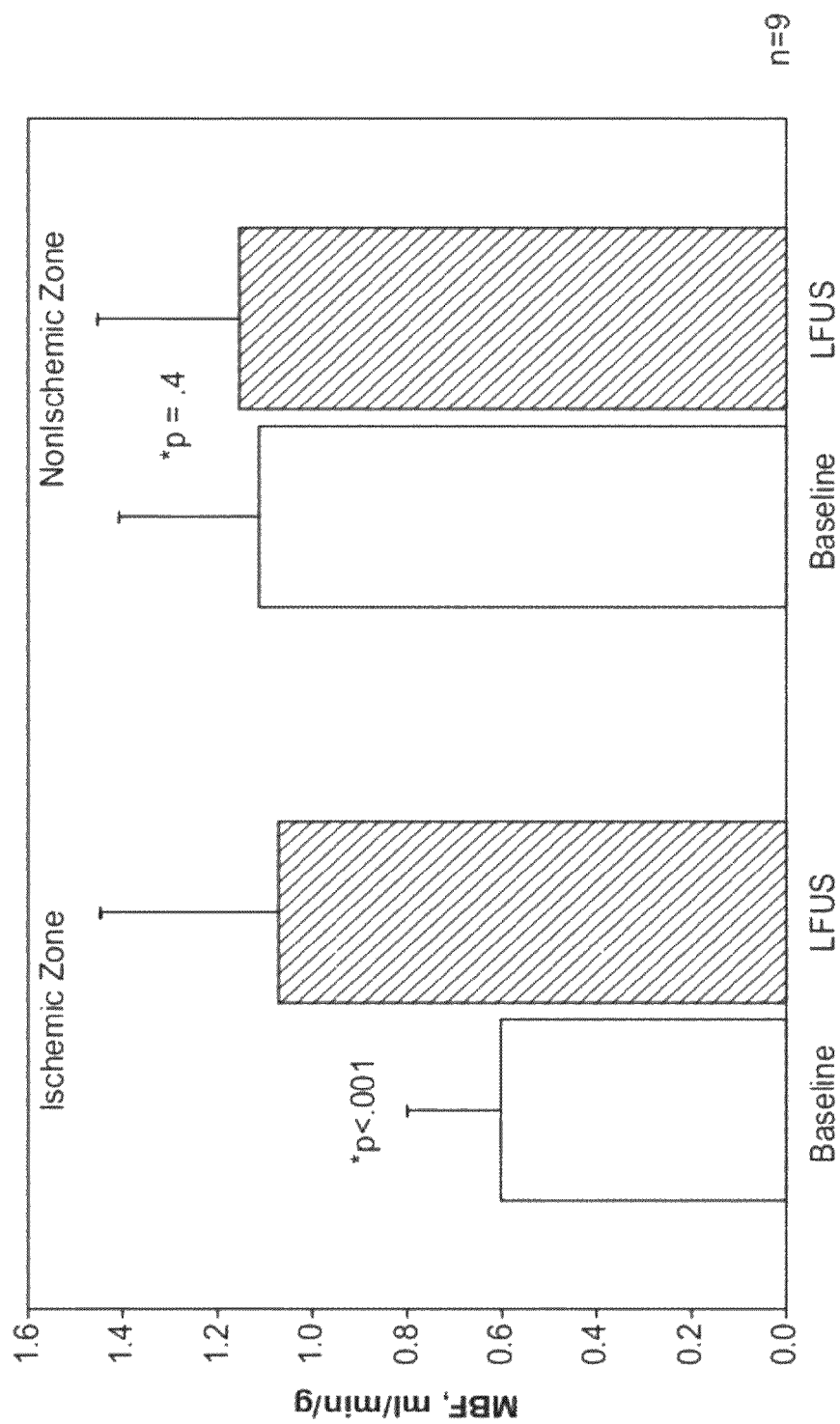
FIG. 1 graphically illustrates absolute myocardial blood flow in ischemic and nonischemic myocardium before and after the application of low frequency ultrasound (LOFUS), indicating that LOFUS increases perfusion.

The present invention provides improved devices, systems, and methods for treatment kidneys and other tissues of the body. The structures and techniques provided often employ cyclical mechanical pressure energy, most often in the form of non-ablative low frequency ultrasound energy. The energy may be at energy levels that are sufficiently low that no therapeutically significant heating of the tissues are generated, but with the energy penetrating into target tissues at levels that are sufficient to induce shear stress. While embodiments of the invention may employ energy focusing structures, the exemplary embodiments do not rely on focusing of the therapeutic energy so that the energy density adjacent the transducer or other energy transmitting surface will often be at least as high as the energy at the target tissue. Nonetheless, the energy levels are sufficiently low as to be safe for intervening tissues between the target tissue and the transducer. Hence, while catheter-based or other minimally invasive probes or systems may be employed (for example, via a minimally invasive aperture site, a natural orifice, and/or the like) in some embodiments, and while even open surgical techniques or transmission of the energy from implants might be employed in other embodiments, many embodiments may make use of non-invasive transducers and the like to transmit the therapeutic energy from outside the patient, through the skin and any intervening tissues so as to provide therapeutic benefits without imposing trauma so as to access the target tissues.

The devices, systems, and methods described herein may be employed to treat a variety of tissue structures so as to ameliorate a wide variety of disease states. Embodiments of the invention may be particularly well suited for treatment of diseases that include an ischemic component, including coronary artery disease, occlusive diseases of the peripheral vasculature, erectile disfunction, hypertension, diabetes, and the like. The exemplary embodiments may have their most immediate application for treatment of the kidneys. Such embodiments may ameliorate, mitigate, and/or avoid some or all acute or long term injury to tissues of the kidneys. Many of the embodiments may be described herein with reference to inhibiting injury to the kidneys associated with administration of contrast imaging agents, and/or in conjunction with dialysis treatment so as to inhibit progression of chronic kidney disease. Nonetheless, the structures and techniques described for these indications will often be suitable for additional therapies as can be understood with reference to the disclosure herein.

The timing for the treatments described herein may, at least in part, be determined based on timing of other treatments. For example, when contrast agents will be used as part of an imaging procedure, it will often be beneficial to have at least a portion of the therapeutic energy delivered to the target tissue within two days, and ideally within one day of the administration of contrast, Exemplary embodiments may benefit from having the energy delivered within 12, 4, or even 2 hours of the administration of contrast, and there may be benefits to treatments that include energy delivery components that occur during at least 2 of: before administering contrast, during administering of contrast, and after administering contrast (with some embodiments including all three). As another example, dialysis patients often undergo regular repeated treatments, with each dialysis treatment lasting well over an hour. These dialysis treatments are generally associated with the past and ongoing injury that the kidneys of the patient have suffered. As the system for application of energy will often be compatible with concurrent dialysis treatments, it will often be desirable to have the energy delivery overlap with the dialysis treatment. Note that the overlap need not be complete for either treatment, so that portions of one or both may occur outside the treatment time of the other. Nonetheless, the overlap can help decrease the impact of the disease on the life of the patient. Still further alternatives may be employed, including a series of energy delivery treatments that occur with at least some of the treatments being scheduled independent of any other therapy. For example, treatments of the heart, kidneys, or other target tissues may be scheduled so as to provide a regular overall treatment energy time (the times often being in a range from ½ hour to 6 hours, for example, a 90 minute treatment) at generally regular intervals (often providing one or more treatment each month or week, for example, treatments three times a week) for a desired number of treatments (optionally being continuous for chronic conditions, but often being between 4 and 50 treatments, such as 36 treatments).

Numerous drugs and other substances are known to be nephrotoxic. For example, radiographic contrast media (e.g. "contrast agent" or "dye"), non-steroidal anti-inflammatory drugs (NSAIDS), amphotericin, methotrexate, acyclovir, gentamicin, acetylcholinesterase inhibitors, other nephrotoxic drugs, products of tumor lysis and products of rhabdomyolysis are known to cause damage to the kidneys.

In particular, radiologic contrast agents, or contrast media, are frequently administered to patients undergoing radiographic investigations, such as X-ray, magnetic resonance and ultrasound imaging, to enhance the image contrast in images of a subject. For example, contrast medium may be administered to patients undergoing coronary angiography, other cardiac catheterization procedures, or computerized tomographic imaging (contrast enhanced CT). Delivery of the contrast media into a patient's vasculature enables different organs, tissue types, or body compartments to be more clearly observed or identified. Examples of contrast agents that might benefit from expanded and/or safer use via the treatment methods and devices described herein include: Visipaque® (iodixanol), Isovue® (iopamidol), Optiray® (ioversol), Omnipaque® (iohexol), and/or Ultravist® (iopromide).

However, the use of radiocontrast media may be associated with adverse side effects, including nephrotoxicity. In particular, contrast medium-induced nephrotoxicity may be an iatrogenic cause of acute renal failure in some patients. In fact, use of contrast media may be the third most common cause of new onset renal failure in hospital patients. Patients who experience nephrotoxicity may experience changes in serum creatinine, or creatinine clearance, at about one to five days after exposure to contrast medium. Consequences may be dramatic and can lead to irreversible renal damage and the need for dialysis, or death.

Acute deterioration in renal function can occur after contrast exposure, particularly for patients with pre-existing renal insufficiency. For patients with abnormal baseline renal function, the incidence of progressive deterioration may be as high as 50%. For hospitalized, critically ill patients, these results may carry a poor prognosis for the patient, especially if dialysis becomes necessary. Factors that may predispose a patient for developing acute renal failure include, pre-existing renal insufficiency, diabetes mellitus, cardiovascular disease, including congestive heart failure, aging, and conditions characterized by depletion of effective circulatory volume.

Several mechanisms may be involved in contrast medium-induced nephropathy. After radiographic contrast medium exposure, a brief period of vasodilation may be followed by renal vasoconstriction leading to intense reduction in renal blood flow leading to renal ischemia, and direct toxicity to renal tubular epithelium by reactive oxygen species (ROS). In addition, patients at high risk of developing renal failure, including those with endothelial dysfunction, may not be able to dilate the renal vasculature, and thus experience a prolonged vasoconstrictive response. Vasoconstriction may not only cause a decrease in renal blood flow and glomerular filtration rate, but it may also exacerbate medullary ischemia by decreasing oxygen supply since renal oxygen consumption is coupled to renal blood flow.

Current methods attempting to reduce or prevent contrast medium-induced renal failure have included periprocedural hydration, forced diuresis, blood volume expansion, low osmolality versus high osmolality contrast agents, dopamine, calcium channel blockers, mannitol, atrial natriuretic peptide, acetylcholine esterase (ACE) inhibitors, the adenosine antagonist theophylline, endothelin receptor antagonists, and N-acetylcysteine. The attempts have generally been directed to reduce vasoconstriction and the negative effects that may be associated with vasoconstriction, such as the exacerbation of medullary ischemia. Contrast media-induced nephropathy appears to remain a leading cause of iatrogenic acute kidney injury, despite adherence to protocols of risk assessment and prevention strategies.

A possible factor in the pathogenesis of contrast induced nephropathy is the induction of endothelial dysfunction and altered renal microcirculation. The endothelial dysfunction may be associated with a contrast media-induced downregulation of renal cortical and medullary nitric oxide (NO) synthesis by endothelial nitric oxide synthase (eNOS). NO may function as a vasodilator and "endogenous diuretic" which regulates medullary perfusion, salt and water handling by adjacent nephrons, and may prevent ROS-mediated endothelial cell injury and blunt flow- and transport-dependent ROS formation in kidney cells. eNOS may be localized to renal vascular endothelium and epithelia of certain nephron segments, such as thick ascending loop of Henle. The renal inner medulla, one of the most sensitive regions of the kidney to injury from contrast media, may possess the greatest amount of eNOS enzymatic activity in the kidney.

Protection of the kidney against ischemia-reperfusion injury has been shown following preconditioning of the kidney—several brief cycles of ischemia and reperfusion prior to prolonged ischemia—and post conditioning—several brief cycles of ischemia and reperfusion after reperfusion from prolonged ischemia. Studies have shown that the protective effects of ischemic pre- and post conditioning are mediated by NO production. Hence, methods to enhance NO production in the kidney prior to and following ischemic or toxic insults may provide significant therapeutic potential.

Physiologic Effects of Low-Frequency Ultrasound

Ultrasound is cyclic sound pressure with a frequency greater than the upper limit of human hearing, which is approximately 20 kHz. The use of ultrasound may accelerate fibrinolysis in vitro and in animal models. In experiments using a rabbit femoral artery thrombolysis model, it was observed that muscle distal to a thrombus lost its cyanotic appearance during ultrasound exposure, independent of fibrinolysis and reperfusion of the femoral artery. In other experiments, it was shown that application of 40 kHz ultrasound at low intensity improved perfusion and reversed acidosis in acutely ischemic skeletal muscle through a nitric oxide dependent mechanism. There was a 3.6 fold increase reported in endothelial nitric oxide synthase activity (eNOS) concurrent with ultrasound that was blocked with prior administration of L-NAME, an eNOS inhibitor. Endothelial cell NOS may be activated by several stimuli, including mechanical forces such as shear stress, the likely mechanism related to low frequency ultrasound exposure.

Other experiments showed that low-frequency, low-intensity ultrasound improved tissue perfusion and reversed acidosis in the presence of a fixed coronary occlusion in dog and pig myocardium. The effects were blocked by L-NAME, again, consistent with a nitric oxide (NO)-dependent mechanism. In vitro, cultured endothelial cells exposed to low-frequency ultrasound at low intensities increased NO production through up regulation of eNOS. The response occurred rapidly within 10 seconds of exposure to ultrasound, consistent with activation of latent eNOS by phosphorylation. This potential mechanism is also consistent with the finding that a 385% increase in phosphorylated e-NOS occurred with low-frequency ultrasound applied to ischemic striated muscle in rabbits, without a significant increase in total eNOS expression. The mechanism of ultrasonic NO generation may be related to the endothelium stimulated by shear stress caused by ultrasonication. Ultrasound in the low-frequency range with a frequency generally less than 500 kHz, has excellent tissue penetration with little attenuation or heating, making it well suited for potential clinical applications. The ultrasound can be applied in a pulsed or continuous manner. Low frequency ultrasound of low intensity, generally less than 3 watts/cm$^2$ at a maximum total power output of no greater than 150 watts, is generally non-ablative and generally does not cause an increase in the temperature of the tissue being exposed. Other suitable forms of nonablative, low-intensity mechanical pressure wave energy that may be used to induce shear stress may include low intensity shock wave, optionally using systems derived from those developed by Dornier MedTech, Medispec, or others.

Preliminary data has been obtained to show the effects of external application of pulsed low frequency ultrasound (LOFUS) in the range of 29 kHz, with an on-off duty cycle of of 30%, and power level of 0.4 w/cm$^2$ on myocardial blood flow in patients with regional rest and stress induced ischemia. FIG. 1 shows the results of absolute blood flow, measured with quantitative positron emission computed tomography (PET) imaging. LOFUS reportedly induced a>45% increase in absolute myocardial blood flow in the ischemic region of the heart (0.6±0.2 to 1.1±0.4 ml/min/gm, n=9 pts, p<0.001) with little change in nonischemic regions of the heart (1.1±0.3 to 1.2±0.3, p=ns).

Figures 2, 3:
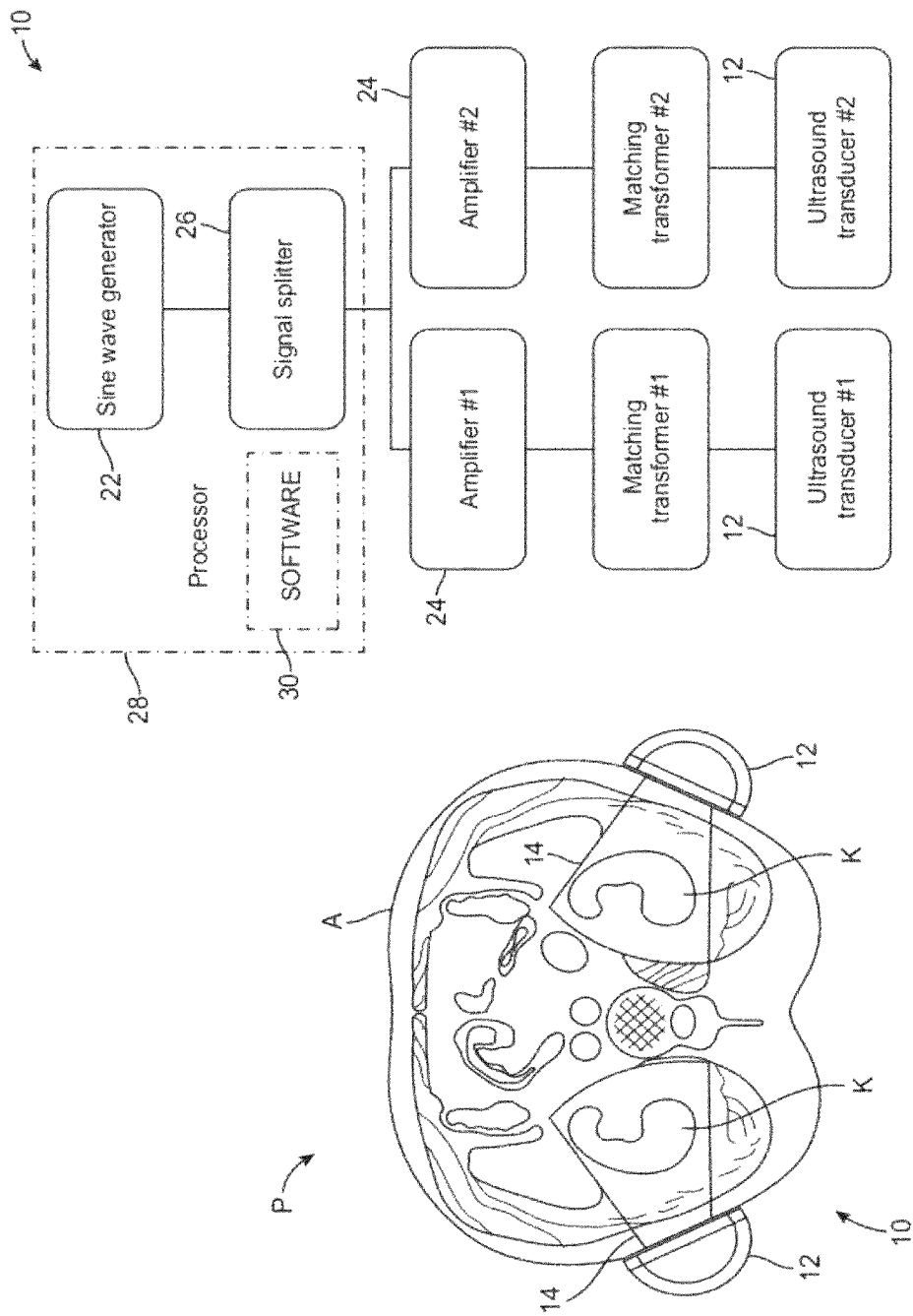
FIG. 2 schematically illustrates a transverse CT image of the abdomen at the level of the kidneys, along with the use of a system to apply unfocused LOFUS to treat against nephrotoxic injury.
FIG. 3 is a functional block diagram of an ultrasound energy system for selectively transmitting LOFUS from two transducers toward two kidneys of a patient.

These results show that low frequency ultrasound increased tissue blood flow in the heart, likely due to the formation of nitric oxide (NO) via a mechanical stimulation of endothelial cells (shear stress) secondary to LOFUS. Unlike the heart, where changes in blood flow may be directly coupled to changes in cardiac function, the standard cardiac applications of therapy to improve blood flow may not apply to the kidney. Enhanced blood flow may not be sufficient to protect the kidney, where complex functions such as filtering the blood and producing urine occurs. Nitric oxide, however, may have protective effects on a variety of processes in the kidney. Embodiments of the proposed invention include the external application of low frequency ultrasound to protect the kidney against injury, by inducing shear stress and causing phosphorylation of endothelial nitric oxide synthase to increase the production and release of NO in the kidney, prior to, during, or following the administration of toxic nephrotoxic substances, such as radiocontrast media. One example is to apply LOFUS prior to, during, and or following the administration of contrast material to patients undergoing CT imaging of various organs. Application of LOFUS may occur with the patient sitting, or lying supine, or lying in the prone position. Another example is to apply LOFUS prior to, during, or following the administration of contrast media to patients undergoing diagnostic or therapeutic angiographic procedures in the catherization laboratory, including cardiac and interventional radiology. FIG. 2 schematically illustrates the placement of two ultrasound transducers in alignment with the kidneys, along with delivery of low frequency ultrasound energy to each kidney to provide a therapeutic response. More specifically, FIG. 2 is a schematic of a transverse CT image of the abdomen A of a patient P at the level of the kidneys K using a system 10 to apply unfocused LOFUS to treat against nephrotoxic injury. The system 10 may comprise two tranducers 12 to separately administer LOFUS to each kidney. The transducers supply nonablative, penetrating energy 14, often without the measurement of a reflection signature to be used for imaging. System 10 may allow simultaneous or separate control of both transducers.

Transducers 12 may be built into a sitting device to allow application of energy while the patient is sitting. The transducers may be built into a table to allow the patient to be treated while lying either supine or prone. The transducers may be built into a device that can be worn by the patient. When used to ameliorate injury from contrast media, some or all of the structural body supporting the transducers can be configured to accommodate imaging. Optionally, the body may have an imaging window (such as an opening or material that is transparent for imaging through) to allow imaging of the heart or other tissue structure of interest. The system may have a separate set of transducers to allow imaging of structure or measurement of blood flow either intermittently or simultaneously during the application of low frequency therapeutic energy. System 10 may have devices available to monitor physiologic parameters such as heart rate, blood pressure, or ECG.

A wide variety of alternative systems and/or alternative system components might be used. The system may have transducers built into catheters that can be placed into the vasculature of the kidneys or other organs such as the heart, liver, or brain to supply nonablative, penetrating energy internally to the organ. The treatment may be done acutely prior to, during, or following administration of toxic substances such as contrast media, or the treatments may be done over a prolonged period of time, including but not limited to minutes, days, weeks, or months. The system may incorporate transducers that can be worn by the patient to allow external multiple treatments over time, including but not limited to minutes, days, weeks, or months. The system may be used to treat one organ, such as the heart, to provide protection for a remote organ, such as the brain, liver, or kidney. The system may be used to protect against organ injury due to reduced blood flow, or ischemia, in organs such as the heart, brain, kidney, or liver. The system may be used to supply nonablative energy to reduce the injury to organs due to ischemia, either prior to restoration of blood flow or reperfusion, or after restoration of blood flow. The system may be used to reduce organ injury in conditions such as acute myocardial infarction, ischemic or hemorrhagic stroke, or used during cardiac arrest to protect the heart and provide remote protection to the brain.

Referring now to FIG. 3, along with one, two, or more transducers 12, system 10 will typically include a signal generator 22 and one or more amplifiers 24, and the like so as to energize the transducers with an appropriate electrical signal so as to cause them to transmit the desired energy to the target tissue. Signal generator 22, amplifiers 24, a signal splitter or multiplexer 26, and/or other electrical components of system 10 will often be coupled to and/or integrated with a processor 28 so as to facilitate control over the energy level, time, duty cycle(s), and the like, as well as to monitor and/or record functioning of the components and delivery of the treatment to the patient.

Processor 28 may comprise (or interface with) a conventional PC system including the standard user interface devices such as a keyboard, a display monitor, and the like. Processor 28 will typically include an input device such as a magnetic or optical disk drive, an internet connection, or the like. Such input devices will often be used to download a computer executable code and processor 28 will often be configured for storage of that code in a tangible storage media 30, with the media embodying any of the methods of the present invention. Tangible storage media 30 may take the form of a floppy disk, an optical disk, a data tape, a volatile or non-volatile memory, RAM, or the like, and the processor 28 will include the memory boards and other standard components of modern computer systems for storing and executing this code. Tangible storage media 30 may optionally embody data associated with the patient and/or treatment. While tangible storage media 29 will often be used directly in cooperation with a input device of processor 22, the storage media may also be remotely operatively coupled with the processor by a network connections such as the internet, and/or by wireless methods such as infrared, Bluetooth, or the like.

System 10 is shown in FIG. 3 as having a single signal generator 22 for generating a signal that can be selectively directed to one or more of the transducers 12 under the direction of processor 28. An Agilent 33220 sine wave generator or the like may be used as signal generator 22. The signals are amplified and the amplified signals are sent to matching transformers before being transmitted to ultrasound transducers. A wide variety of transducers might be employed, with suitable transformers optionally including PZT 4, 8, or the like, as may be commercially available from Morgan Matroc or other vendors. Suitable transducers may also include (or be derived from) those that were previously developed by Timi3 Systems Inc. of Santa Clara; those that have been developed by Cybersonics Inc. of Pennsylvania, and from a variety of other sources. Alternative embodiments may employ separate signal generators for each transducer, multiplexing of signals after amplification in coordination with a micro and/or macro duty cycle, or the like. Hence, a wide variety of system architectures might be employed.

Figure 3A:
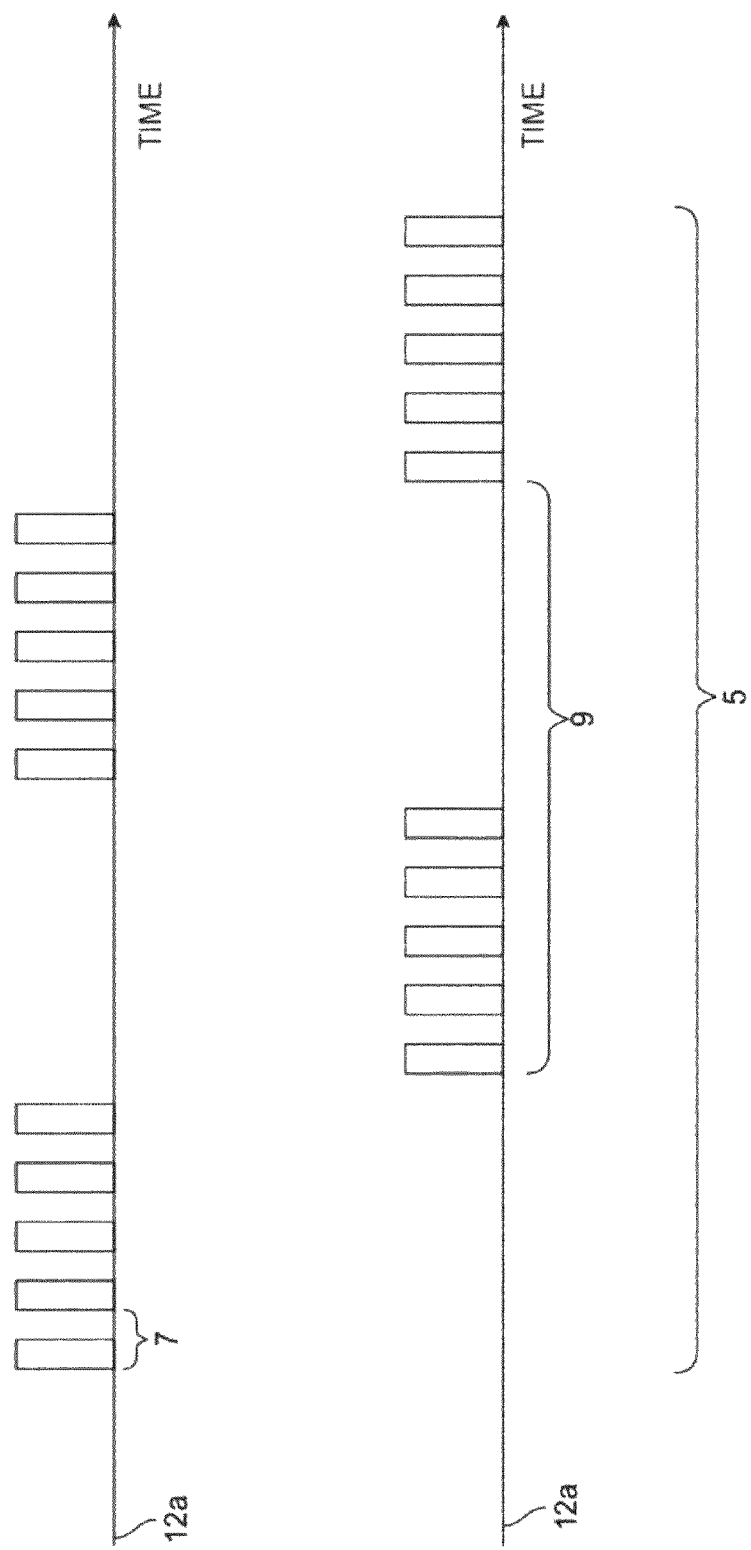
FIG. 3A schematically illustrates superimpose micro and macro duty cycles.

Referring now to FIG. 3A, a combined micro/macro duty cycle is schematically illustrated. A first energizing signal 12a may be supplied by the power source components of system 10 to one or more first transducer 12 oriented toward a first kidney, such as transducer #1. A second energizing signal 12b may be supplied to one or more second transducer 12, such as transducer #2. The overall treatment period 5 encompasses a number of on/off cycles for each transducer (or transducers, when more than one transducer is oriented toward each kidney). The energized cycles are defined by two different time periods. First, each transducer is pulsed rapidly on and off per a relatively short cycle time period 7. This is sometimes referred to herein as a micro duty cycle, and will often make use of a duty cycle time period of less than a second, so that the micro duty cycle may have a frequency of 1 Hz or more, ideally being between 20 Hz and 50 Hz. Second, the overall treatment period 5 also encompasses a series of second time periods 9, with the second time periods generally being longer than 1 minute, ideally being between 2 and 30 minutes. Each transducer is energized (with pulsed energy per the micro duty cycle) for only a portion of each macro duty cycle. Hence, the micro duty cycle and macro duty cycle are superimposed on each other.

The illustration of FIG. 3A is a simplified schematic. Only a few micro cycles are shown in each macro cycle for simplicity; there will typically be from roughly 10 to 1000 micro cycles for each macro cycle. Similarly, while one two macro duty cycles are shown in time period 5, typically there will be 3 or more, often being at least 4. Each micro pulse of energy will typically comprise an alternative signal per frequency of the energy being applied (low frequency ultrasound or the like). While two 50% on/off duty cycles are shown (with the "on" times being the same length as the "off" times), alternative embodiments may have lower (or in some cases higher) values for one or both of the duty cycles. Additional details on the micro duty cycle for a single transducer (as may be modified for use in the devices and systems described herein) can be understood with reference to the publications describing the LOFUS system developed by Timi 3 Systems Inc of Santa Clara, including U.S. Pat. No. 7,241,270, the full disclosure of which is incorporated herein by reference. Advantages of the superimposed macro duty cycle may include increased safety, tissue recovery allowing enhanced and/or more sustained NO release via enhanced enzymatic activity, and the like.

Figure 4A:
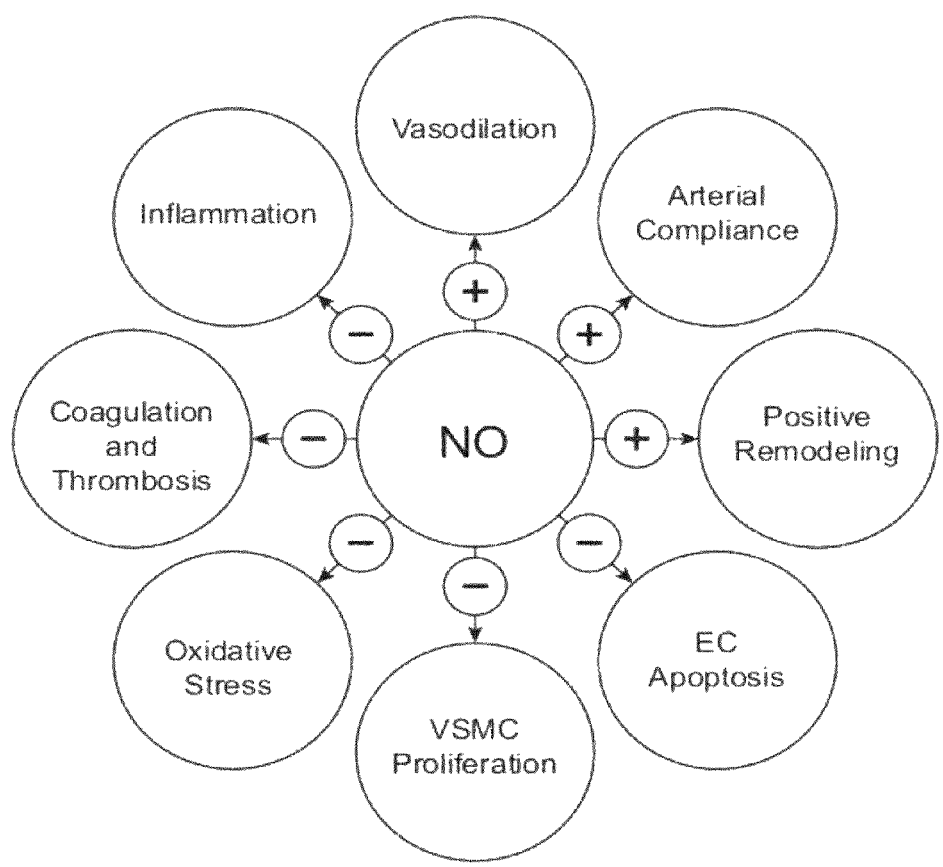
FIG. 4A schematically illustrates physiological functions of nitric oxide (NO)
Figure 4B:
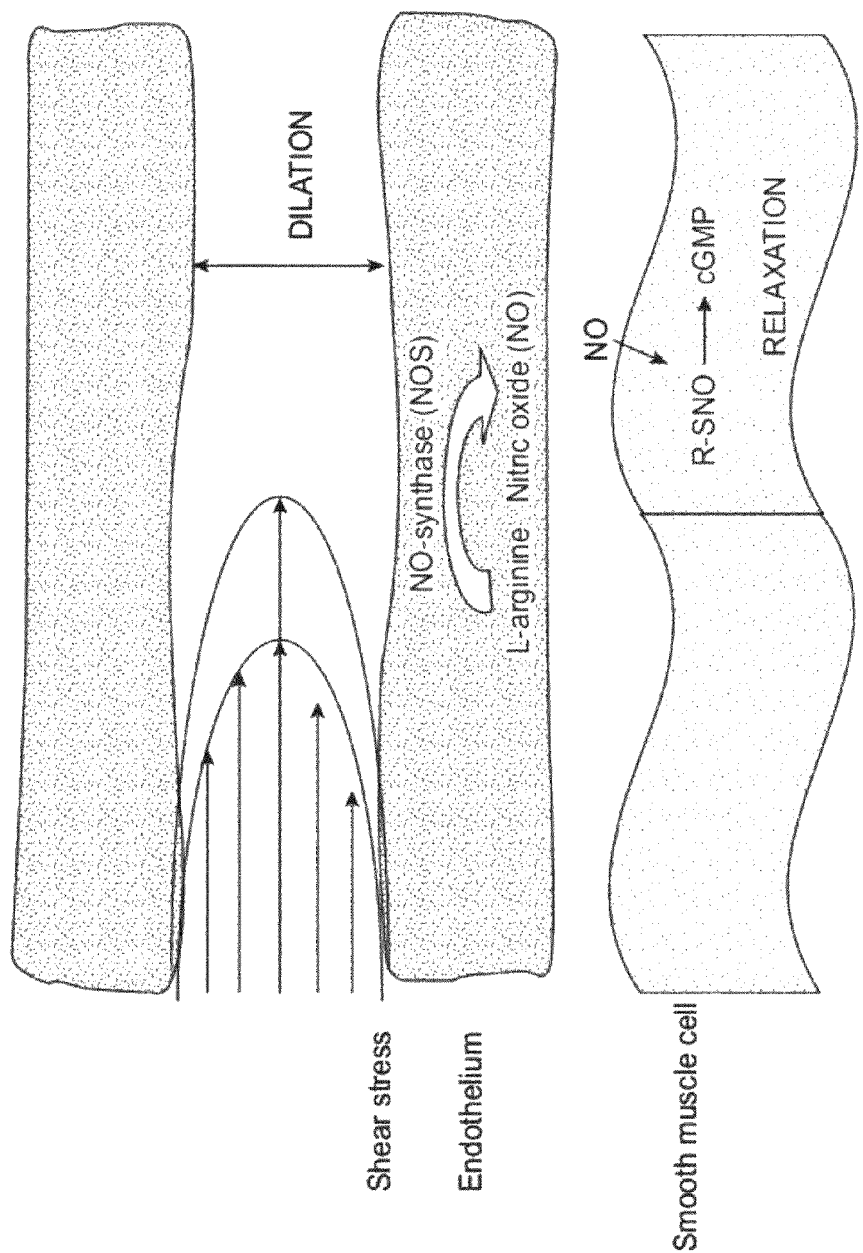
FIG. 4B schematically illustrates NO production induced by shear stress, such as the shear stress caused by LOFUS.

FIG. 4A schematically illustrates some of the physiological functions of Nitric Oxide (NO). When released in the target tissue in response to the energy applied by system 10, NO may inhibit inflammation, coagulation and thrombosis, oxidative stress, proliferation of vascular smooth muscle cells (VSMCs), and/or endothelial cell (EC) apoptosis. This NO may also promote, within the target tissue and in response to the energy from system 10, vasodilation, arterial compliance, and/or positive remodeling. A pathway for production of NO within the kidney using shear stress induced by the energy from system 10 is schematically illustrated in FIG. 4B. Additional information on shear stress-induced NO and the pathway illustrated in FIG. 4B can be found in De Groot P, Bleeker M, Hopman M. *Magnitude and time course of arterial vascular adaptations to inactivity in humans*, Exerc Sport Sci Rev. 2006; 34(2): 65-71.

Figure 5:
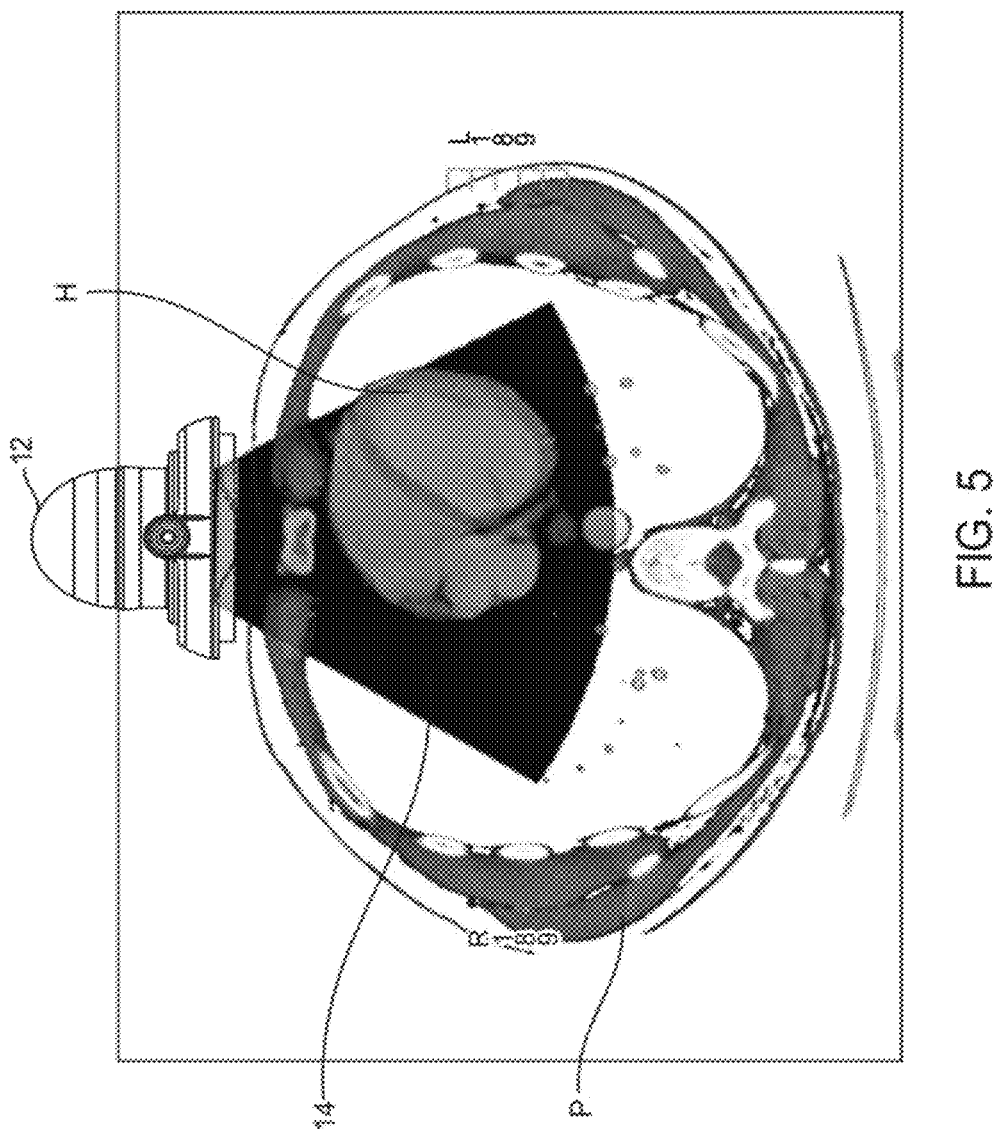
FIG. 5 schematically illustrates a LOFUS myocardial therapy.
Figure 5C:
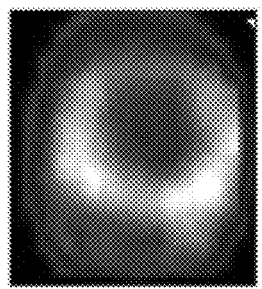
FIG. 5A-5D illustrate increases in perfusion in ischemic myocardium resulting from LOFUS, with FIGS. 5A and 5B showing perfusion prior to application of LOFUS and FIGS. 5C and 5D showing perfusion after application of LOFUS.
Figure 5D:
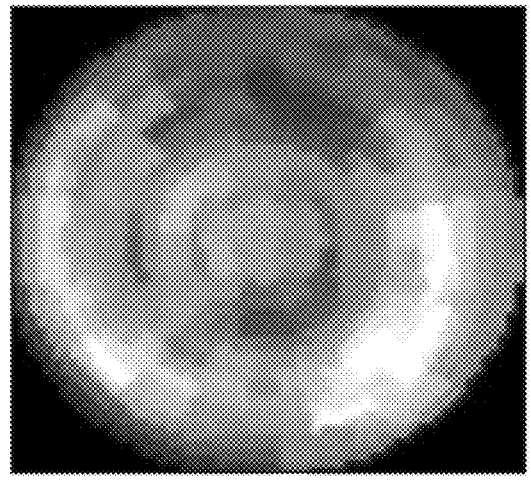
Figure 5A:
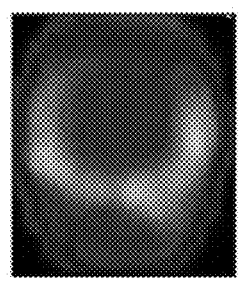
Figure 5B:
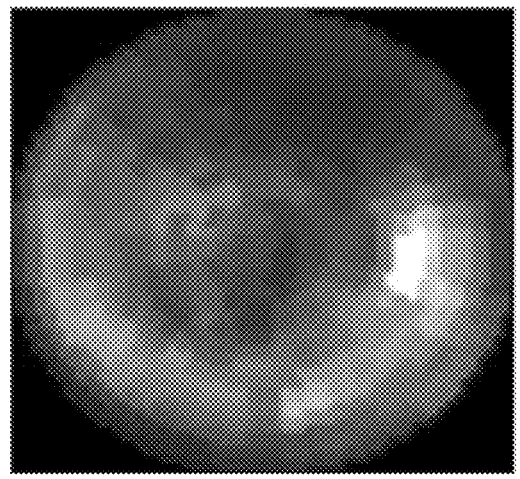

Referring now to FIG. 5, application of LOFUS energy 14 from a transducer 12 to a heart H of a patient P is schematically illustrated. Measured myocardial blood flows before and after the application of LOFUS energy are shown in FIGS. 5A and 5B (before) and FIGS. 5C and 5D (after). The blood flows were measured using Rb-82 positron emission computed tomography (PET) imaging before and after low frequency ultrasound in 4 patients with resting myocardial ischemia (hibernating myocardium), and 5 patients with stress induced ischemia. FIGS. 5A and 5C show images of the heart in short axis, and FIGS. 5B and 5C show polar maps, with greater blood flows generally corresponding to lighter portions of the image. Both the pre-LOFUS (FIGS. 5A and 5B) and post-LOFUS (FIGS. 5C and 5D) images were taken from a single patient with myocardial ischemia at rest. As can be seen by comparing the images, there was an increase in regional blood flow in the lateral wall following low frequency ultrasound treatment. The overall results of these measurements are graphically summarized in FIG. 1, as described above.

Figure 6:
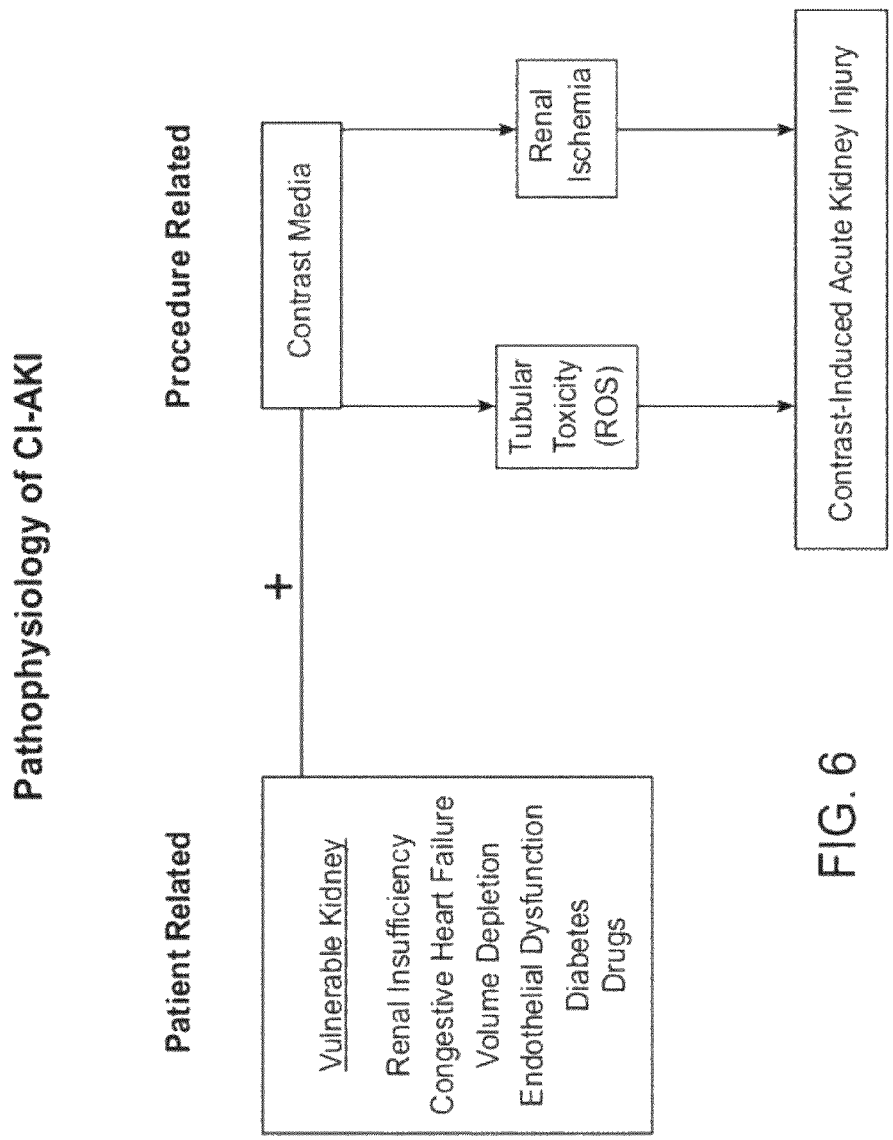
FIG. 6 schematically illustrates the pathophysilogy of contrast induced acute kidney injury (CI-AKI)
Figure 7:
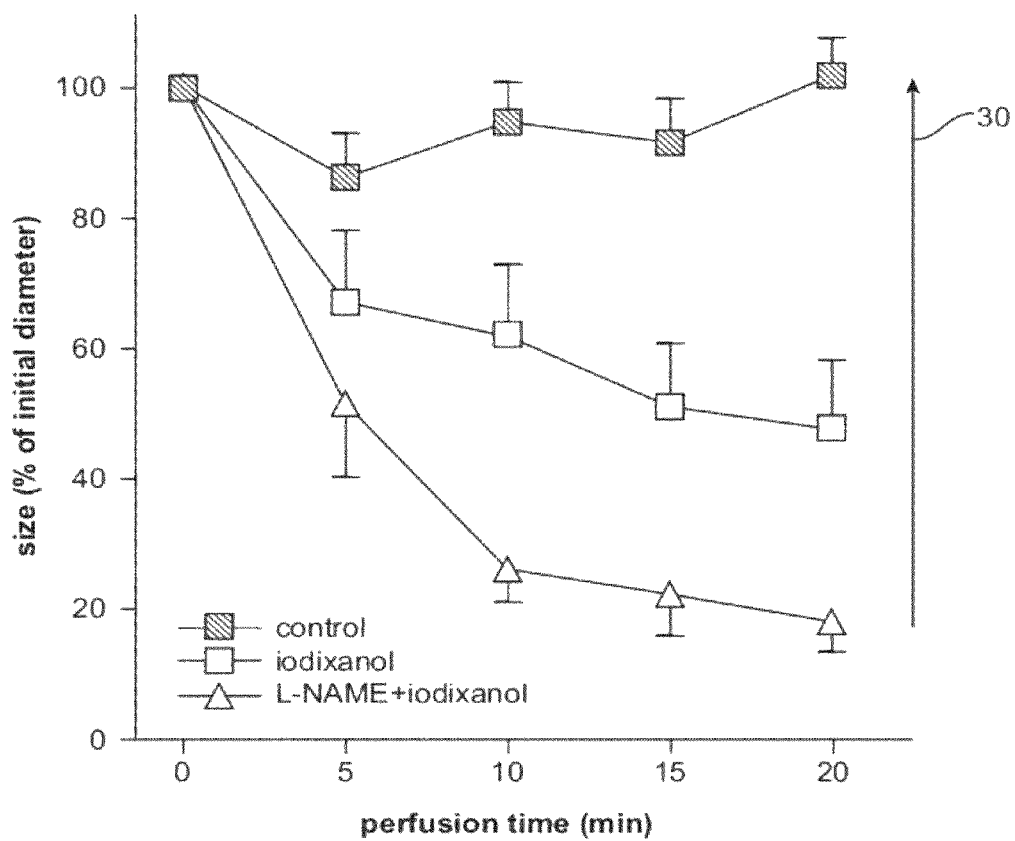
FIG. 7 graphically illustrates a model of vasodilation effects of NO as may be released in the kidneys by the application of LOFUS.

FIG. 6 schematically illustrates the pathophysiology of CI-AKI, as generally described above. FIG. 7 FIG. 1 shows evidence of vasoconstriction upon exposure to contrast media, which is further enhanced by inhibition of enthothelial nitric oxide synthase by L-NAME. While the results shown in FIG. 7 are based on vessel constriction, they are consistent with the ability of LOFUS from system 10 to induce vasodilation, increasing the diameter of the vessels of the target tissue as schematically illustrated by arrow 30. Additional understanding of the experimental basis for the vasoconstriction and potential dilation of vessels by release of NO may be avialable in Sendeski M, Patzak A, Pallone T, Cao C, Persson A, Persson P:Iodixanol, constriction of medullary descending vasa recta, and risk for contrast medium-induced nephropathy. Radiology 2009; 251:697-704.

Figure 8:
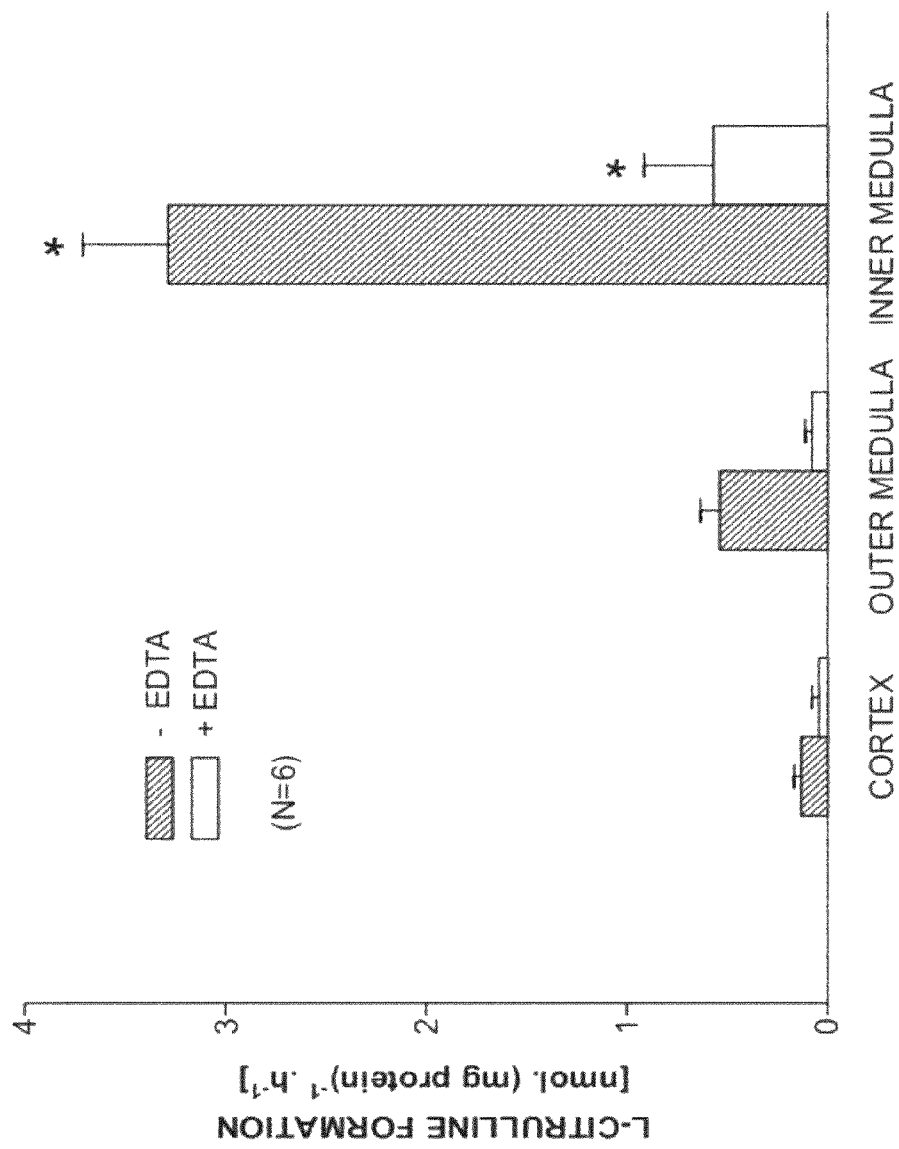
FIG. 8 graphically illustrates local availability of NO within the kidney, as may be released via the application of LOFUS.

Referring now to FIG. 8, the kidney is generally prone to hypoxia, with the medulla being particularly susceptible. Fortunately, the inner medulla also includes the highest content of eNOS within the renal medulla, so that this tissue is particularly well suited to release NO and thereby benefit from the LOFUS energy from system 10. Additional details regarding the measurments represented by FIG. 8 can be seen in Wu F, Park F, Cowley A, Mattson D: Quantification of nitric oxide synthase activity in microdissected segments of the rat kidney. Am J Physiol 1999; 276:F874-F881.

Figure 9B:
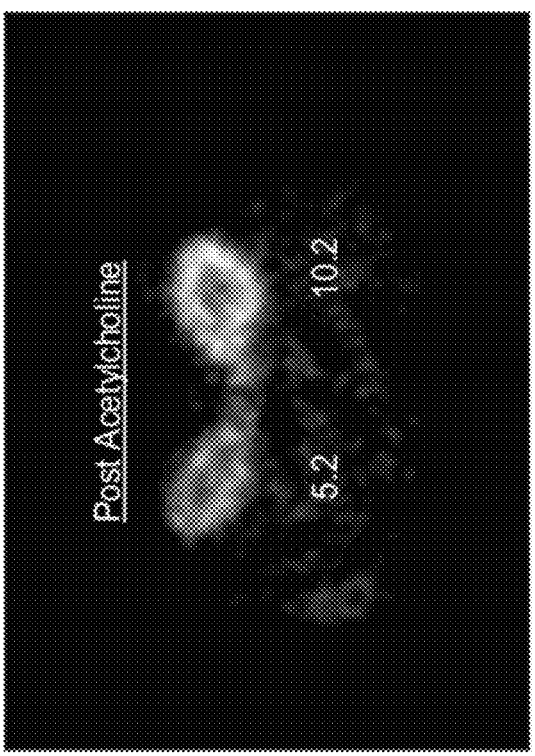
FIGS. 9A and 9B graphically illustrate a model of renal bloodflow effects on perfusion that may be induced by the application of LOFUS.
Figure 9A:
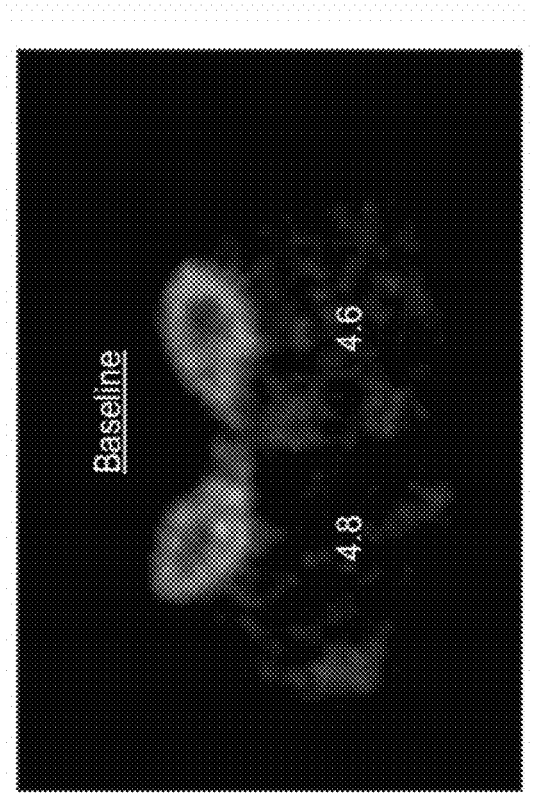
Figure 10:
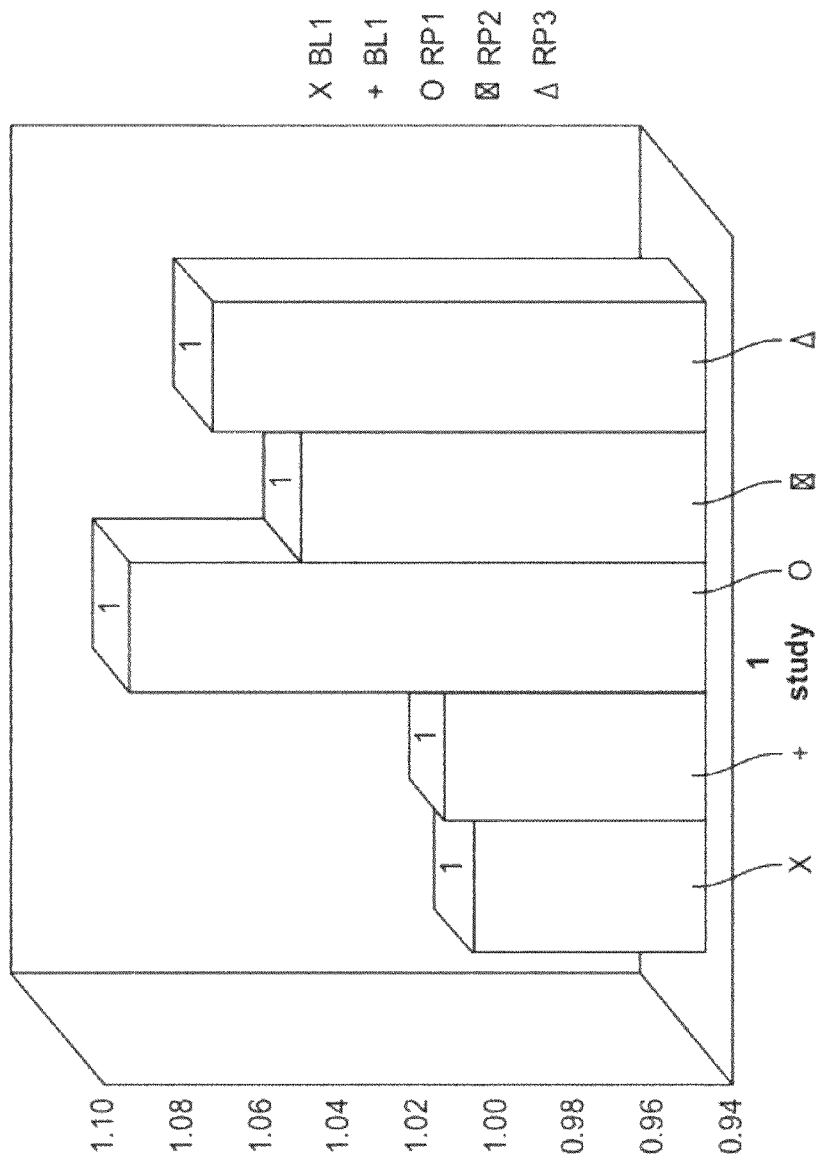
FIG. 10 graphically illustrates renal bloodflow measurements before and after application of LOFUS.

FIGS. 9A and 9B show measured renal blood flow using Oxygen-15 water PET imaging before and after intrarenal infusion of acetylcholine, an endothelial dependent renal vasodilator. FIG. 9A shows baseline renal blood flow prior to the infusion, while FIG. 9B shows renal bloodflow following infusion of acetylcholine into the right kidney in a pig. Renal blood flows are shown in ml/min/gm, and more than doubled in the right kidney in response to the infusion. Unfortunately, dilation agents have often shown systemic toxicity when used in sufficient doses to affect kidney function. Localized infusion into the kidney requires invasive procedures in the catheterization laboratory, and may not be suited for outpatient use. In contrast, FIG. 10 shows relative values of left kidney renal blood flow before LOFUS (BL) and following LOFUS (RP). Hence, the use of system 10 provides a noninvasive solution with applicability in a wide range of clinical situations for acute and chronic application for kidney protection.

Figure 11:
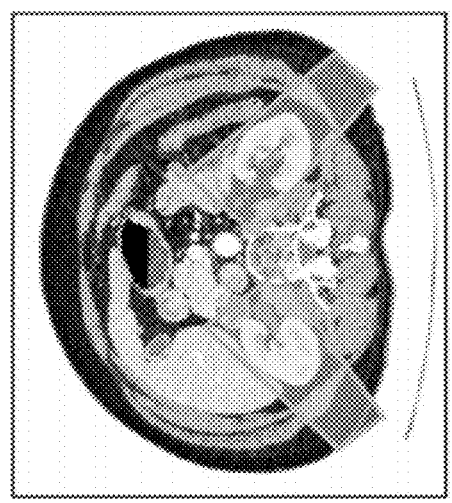
Figure 12B:
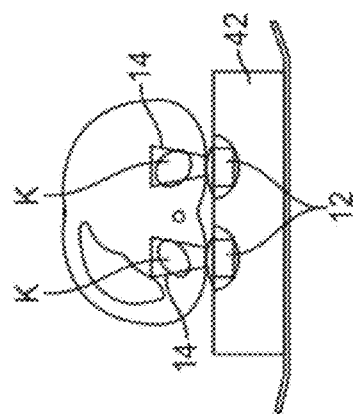
FIGS. 12A and 12B schematically show a table structure supporting a patient and orienting transducers of the ultrasound system toward the kidneys.
Figure 12A:
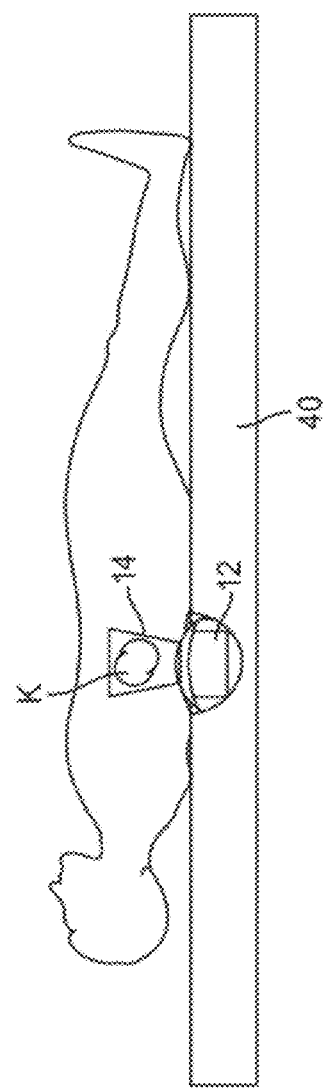

FIG. 11 schematically shows a CT scan of the abdomen with a zone of sonication arising from transducers aligned with each kidney. As can be understood with reference to FIGS. 12A and 12B, transducers 12 may optionally be mounted to a patient support structure or body such as a table 40, a pallet 42 to be placed on a surgical table, or the like. Transducers 12 may include a fluid-filed chamber with a flexible membrane or patient interface positioned and configured relative to the patient support surface so as promote coupling of the transducers with the skin of the patient, the fluid and interface generally providing vibrational coupling of the skin and other tissues of the patient with pressure-signal transmitting surfaces of the transducers. The table or other patient support structure may have a centerline or the like, and ultrasound or other imaging systems can be included in system 10 or a separate sonography system can be used to help ensure that the transducers and LOFUS energy are aligned with the tissues of the kidney. As can be seen in FIGS. 12A and 12B, kidneys K may be longer along the sagittal plane than they are wide, and it will often be desirable for the energy to encompass some or all of the medulla and or kidney itself. Hence, it may be beneficial to vary the spatial distribution of the zone of sonication for treatment of the kidneys from a simple circular transducer approach. This elongate special distribution may be effected by reshaping the transducer beam, or using multiple transducers in alignment with each kidney.

Figure 13C:
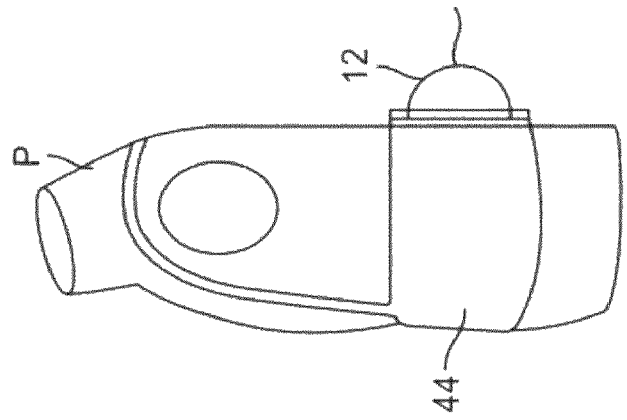
FIGS. 13A-13C schematically illustrate a garment worn by a patient and orienting transducers of the ultrasound system toward the kidneys.
Figure 13B:
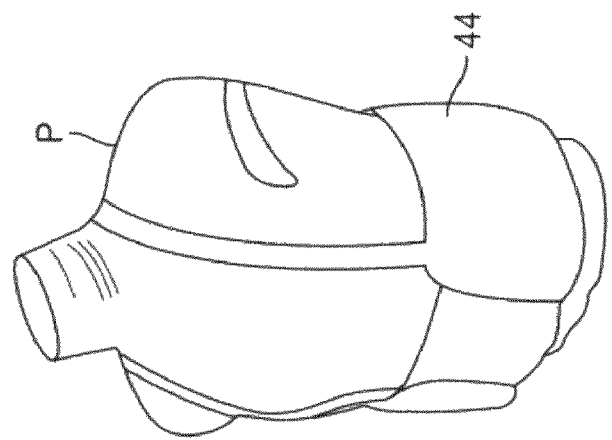
Figure 13A:
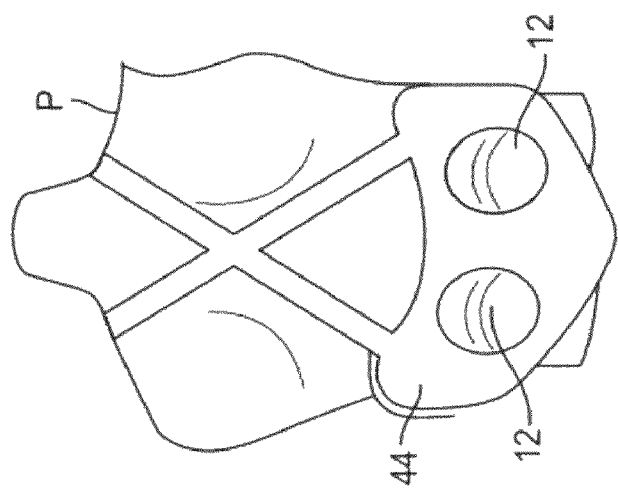
Figure 14B:
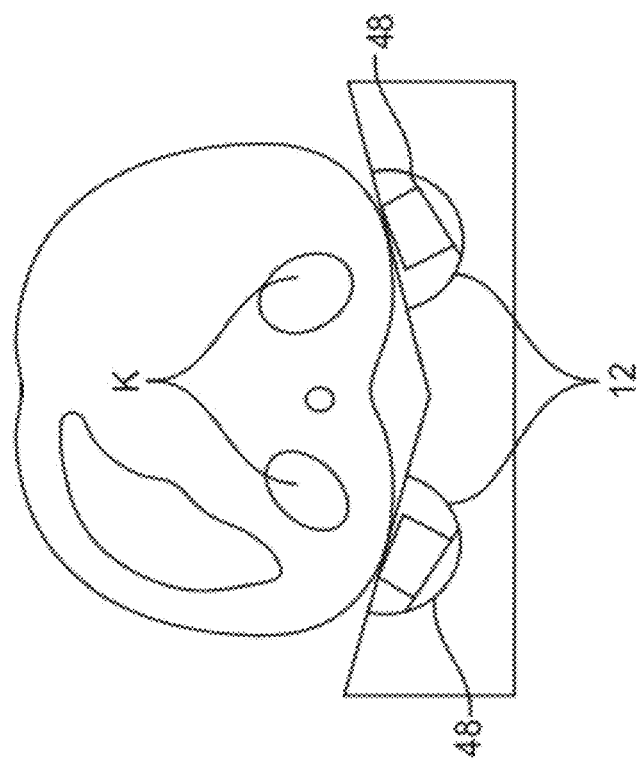
FIGS. 14A and 14B schematically illustrate an alternative support body for orienting transducers toward the kidneys.
Figure 14A:
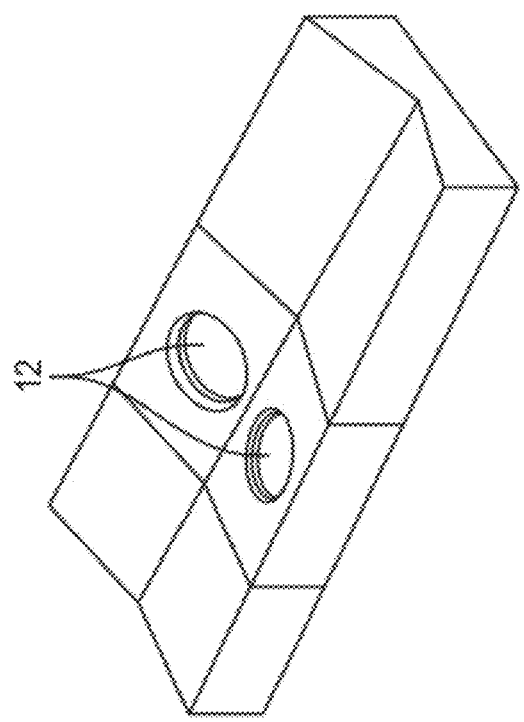

A wide variety of support structures may help maintain alignment between transducers 12 and the kidneys or other target tissues of patient P. In the back, perspective, and side views of FIGS. 13A-13C, respectively, a garment allows at least some mobility of the patient during treatment. More generally, the support structures will often receive the patient so as to be able maintain alignment between the patient and the support structure. The support structure will also often support the transducers, often allowing some change in position of the transducers relative to the patient and/or each other so as to allow the system to adapt to differing physiologies of differing patients. As can be understood with reference to FIGS. 11, 14A, and 14B, embodiments of support bodies may optionally provide or allow a relative angle between the LOFUS energy, with the transducers optionally being supported via a spherical surface 48 of the body to facilitate varying the angle of one or both transducers.

Figure 15:
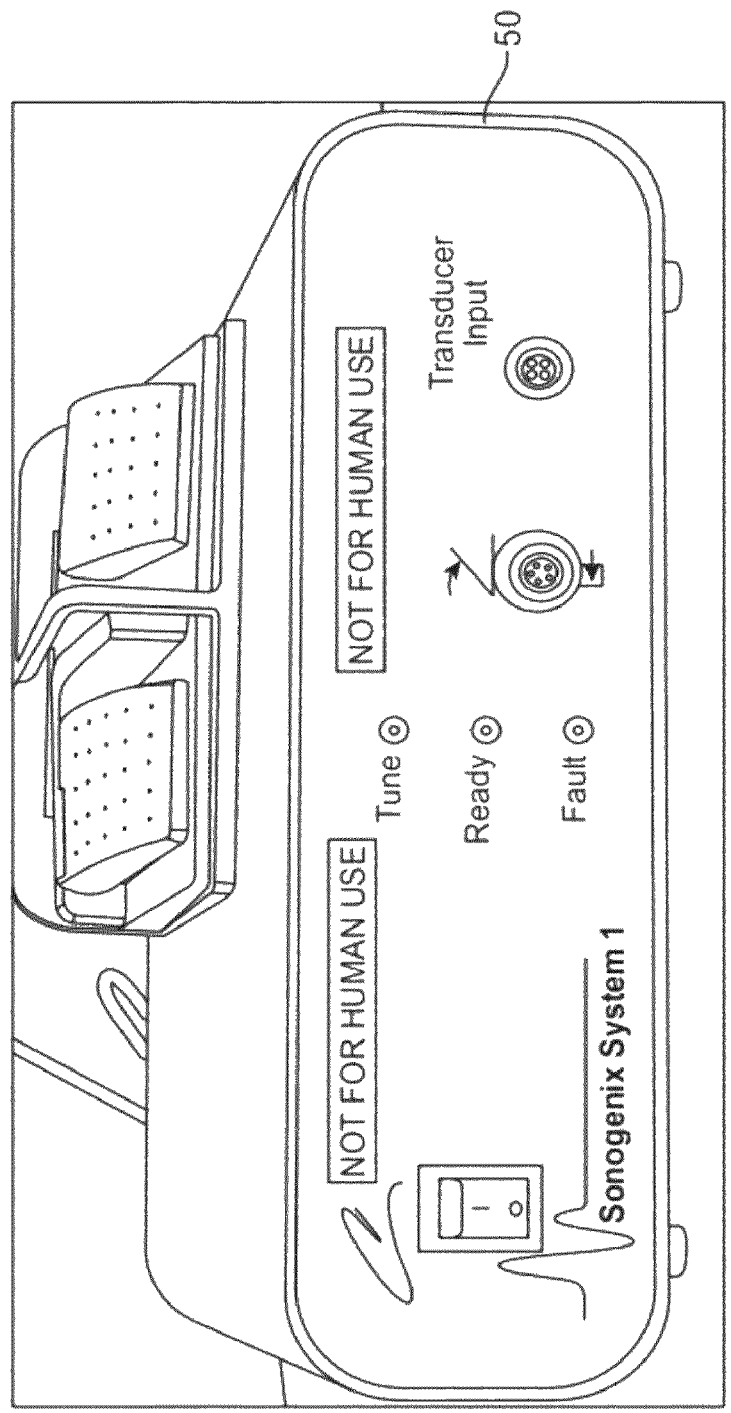
FIG. 15 illustrates a LOFUS ultrasound energy generator for use with one or more transducers for treatment of the kidneys.

Referring now to FIG. 15, an exemplary signal source 50 of system 10 can be seen. Exemplary transducer model 60 is seen in perspective and cross-sectional views in FIGS. 17A and 17B, respectively, while an exemplary physical transducer 62 can be seen in FIG. 16.

While much of the discussion above has emphasized the use of system 10 for dialysis and mitigating nephrotoxicity of contrast agents and other materials, the structures and methods described herein may find a variety of additional applications. For example, chronic kidney disease is often characterized by an activated sympathetic nervous system (SNS), which may contribute to the pathogenesis of hypertension. Kidney injury and ischemia increases afferent sympathetic nerve activity to the central nervous system (CNS) and results in increased sympathetic nervous system activation, and increased blood pressure. The increased catecholamines from SNS activation lead to further injury to the kidney in CKD.

The nitric oxide system is a natural antagonist of catecholamines. A state of nitric oxide deficiency is characteristic in CKD patients. Standard hemodialysis causes sympathetic activation. Advantageously, repeated application of LOFUS to patients with CKD may result in a slowing of the progression of CKD, and one strategy to improve kidney oxygenation via increased vasculogenesis might be key component of this protection. Such repeated LOFUS may also provide a reduction in blood pressure in hypertensive patients with CKD (and may also be effective as a noninvasive means of blood pressure reduction in the general population with drug resistant hypertension). Hence, LOFUS may be administered up to daily for up to several hours per day for up to weeks (or even months), using the energy characteristics already described.

In one exemplary approach, 35 one-hour treatment periods with application of LOFUS may be performed for a patient with CKD over about 7 weeks to slow CKD progression. This may invoke the anti-inflammatory properties of NO, and ischemia treating properties of NO (vasculogenesis and cell protection) to provide sustained beneficial effects following a course of repeated therapy.

While exemplary embodiments have been described in some detail, by way of example and for clarity of understanding, those of skill in the art will recognize that a variety of modification, adaptations, and changes may be employed. Hence, the scope of the present invention should be limited solely by the claims.

What is claimed is:

1. A method for treating a patient, the patient having a tissue subject to injury, the method comprising:
   transmitting low frequency ultrasound energy from a transducer to the tissue;
   the energy being transmitted to the tissue during a treatment time period with a treatment energy level per a first duty cycle and a second duty cycle;
   the first duty cycle having a first repetition frequency and the second duty cycle having a repetition frequency different than the first duty cycle;
   the second duty cycle being superimposed on the first duty cycle; and
   the treatment time period and energy level being sufficient to mitigate the injury to the tissue; wherein
   the first repetition frequency defines a plurality of first duty cycle time periods during the treatment time period, the transducer being energized during a portion of each first time period per the first duty cycle throughout a portion of the treatment time period;
   the second repetition frequency defining a plurality of second duty cycle time periods during the treatment time period, the transducer being selectively energized during a portion of each second time period;
   the energized portions of the second time periods are sufficiently longer than the first time periods so that during the energized portion of each second time period the energizing of the transducer repeatedly cycles per the first duty cycle.

2. The method of claim 1, wherein the energy comprises low frequency ultrasound energy with a frequency in a range from about 20 kHz to about 500 kHz, and an intensity of less than 3 watts/cm2.

3. The method of claim 1, wherein the first duty cycle repetition frequency is in a range from about 20 Hz to about 50 Hz, the first duty cycle comprising a micro duty cycle, and the second time period of the second duty cycle is between 2 and 30 minutes, the second duty cycle comprising a macro duty cycle.

4. The method of claim 3, wherein the treatment time period is between ½ hour and about 6 hours.

5. The method of claim 1, the injury including an ischemic injury, the treatment time period and energy level being sufficient to mitigate the ischemic injury to the tissue and being insufficient to ablate the tissue.

6. The method of claim 5, the tissue comprising cardiovascular tissue, the treatment time period and energy level being sufficient to promote perfusion.

7. The method of claim 5, the tissue comprising myocardium, the treatment time period and energy level being sufficient to promote myocardial perfusion.

8. A system for treating a patient, the patient having tissue subject to injury, the system comprising:
   a transducer configured to selectively direct low frequency ultrasound energy to the tissue;
   a power source coupled to the transducer, the power source configured to energize the transducer for a treatment time period and with a treatment energy level per a first duty cycle and a second duty cycle;
   the first duty cycle having a first repetition frequency and the second duty cycle having a repetition frequency different than the first duty cycle;
   the second duty cycle being superimposed on the first duty cycle; and
   the treatment time period and energy level being sufficient to mitigate the injury to the tissue;
   wherein the transducers are included in an ultrasound energy source system, wherein the ultrasound system is configured to transmit the energy as low frequency ultrasound energy with a frequency in a range from about 20 kHz to about 500 kHz, an intensity of less than 3 watts/cm2, and a first duty cycle of 50% or less so that each transducer is energized for only a portion of the treatment time period, the first duty cycle having a first duty cycle repetition frequency greater than the ultrasound energy frequency.

9. The system of claim 8, wherein:
   the first duty cycle repetition frequency defines a plurality of first duty cycle time periods during the treatment time period, the ultrasound system being energized during a portion of each first time period per the first duty cycle throughout a portion of the treatment time period; and
   a second duty cycle repetition frequency defines a plurality of second duty cycle time periods during the treatment time period, the ultrasound system being selectively energized during a portion of each second time interval;
   the second duty cycle is superimposed on the first duty cycle and the energized portions of the second time periods are sufficiently longer than the first time periods so that during the energized portion of each second time period the energizing of the energy source repeatedly cycles per the first duty cycle.

10. The system of claim 9, wherein the first duty cycle repetition frequency is in a range from about 20 Hz to about 50 Hz, the first duty cycle comprising a micro duty cycle, and the second time period of the second duty cycle is between 2 and 30 minutes, the second duty cycle comprising a macro duty cycle.

11. The system of claim 10, the tissue being separated from the skin by intervening tissue, wherein the transducer comprises a non-invasive transducer configured to engage a skin surface of the patient.

12. The system of claim 11, wherein the treatment time period is between ½ hour and about 6 hours.

13. The method of claim 12, the injury including an ischemic injury, the treatment time period and energy level being sufficient to mitigate the ischemic injury to the tissue and being insufficient to ablate the tissue.

14. The method of claim 13, the tissue comprising cardiovascular tissue, the treatment time period and energy level being sufficient to promote perfusion.

15. The method of claim 14, the tissue comprising myocardium, the treatment time period and energy level being sufficient to promote myocardial perfusion.

16. A system for treating a patient, the patient having tissue subject to injury, the system comprising:
   a transducer configured to selectively direct low frequency ultrasound energy to the tissue;
   a power source coupled to the transducer, the power source configured to energize the transducer for a treatment time period and with a treatment energy level per a first duty cycle and a second duty cycle;

the first duty cycle having a first repetition frequency and the second duty cycle having a repetition frequency different than the first duty cycle;

the second duty cycle being superimposed on the first duty cycle such that:

the first duty cycle repetition frequency defines a plurality of first duty cycle time periods during the treatment time period, the ultrasound system being energized during a portion of each first time period per the first duty cycle throughout a portion of the treatment time period;

a second duty cycle repetition frequency defines a plurality of second duty cycle time periods during the treatment time period, the ultrasound system being selectively energized during a portion of each second time interval; and the energized portions of the second time periods are sufficiently longer than the first time periods so that during the energized portion of each second time period the energizing of the energy source repeatedly cycles per the first duty cycle; and the treatment time period and energy level being sufficient to mitigate the injury to the tissue.

\* \* \* \* \*